(12) United States Patent
Sheina et al.

(10) Patent No.: US 8,859,718 B2
(45) Date of Patent: Oct. 14, 2014

(54) SYNTHESIS OF CONJUGATED POLYMERS VIA OXIDATIVE POLYMERIZATION AND RELATED COMPOSITIONS

(71) Applicant: Plextronics, Inc., Pittsburgh, PA (US)

(72) Inventors: Elena E. Sheina, Pittsburgh, PA (US); Chad Landis, Oakmont, PA (US); Venkataramanan Seshadri, Monroeville, PA (US); Christopher T. Brown, Pittsburgh, PA (US); Samuel M. Mazza, Pittsburgh, PA (US)

(73) Assignee: Solvay USA, Inc., Cranbury, NJ (US)

( * ) Notice: Subject to any disclaimer, the term of this patent is extended or adjusted under 35 U.S.C. 154(b) by 0 days.

(21) Appl. No.: 13/656,561

(22) Filed: Oct. 19, 2012

(65) Prior Publication Data

US 2013/0109813 A1    May 2, 2013

Related U.S. Application Data

(60) Provisional application No. 61/550,322, filed on Oct. 21, 2011.

(51) Int. Cl.
C08G 75/06 (2006.01)

(52) U.S. Cl.
CPC ..................... *C08G 75/06* (2013.01)
USPC .............................. 528/380; 525/338; 525/55

(58) Field of Classification Search
USPC .......................................... 525/417; 528/380
See application file for complete search history.

(56) References Cited

U.S. PATENT DOCUMENTS

| | | | | |
|---|---|---|---|---|
| 4,599,194 | A | * | 7/1986 | Frommer et al. ............. 524/401 |
| 4,956,444 | A | * | 9/1990 | Kang et al. .................... 528/220 |
| 4,975,317 | A | * | 12/1990 | Kuhn et al. .................... 442/115 |
| 4,986,886 | A | * | 1/1991 | Wei et al. ....................... 205/419 |
| 2001/0039702 | A1 | * | 11/2001 | Araki ............................ 29/25.03 |
| 2004/0171790 | A1 | * | 9/2004 | Baik et al. ..................... 528/378 |
| 2007/0129534 | A1 | * | 6/2007 | Ohata et al. ................... 528/373 |
| 2009/0253893 | A1 | * | 10/2009 | Rieke ............................ 528/378 |

FOREIGN PATENT DOCUMENTS

| | | | | |
|---|---|---|---|---|
| JP | | 07039477 B | * 5/1995 | ............. C08G 61/12 |
| WO | WO 2011/002927 A2 | | 1/2011 | |

OTHER PUBLICATIONS

Mukoyama et al (Electrochemical dissolution of polythiophene films, J. Electronanalytical Chemistry, 531, 133-139, Aug. 2002).*
Wallace et al. (Conductive Electroactive Polymers, Edition 2nd, pp. 185-1952003).*
Machala et al. (On-substrate polymerization of solution-processed, transparent PEDOT:DDQ think film electrodes with a hydrophobic polymer matrix, Organic Electronics, 12, pp. 1518-1526, Jun. 2011).*
Kang et al (Polymerization and Oxidation of Pyrrole by Organic Electron Acceptors J. Poly. Sci. Part A: Poly Chem., vol. 25 pp. 2143-2153 Aug. 1987).*
Nazzal et al (Molecular Weight Determination of Pyrrole-based Polymer, Pyrrole-based Polymers, J. Chem. Soc. Chem Commun p. 83-84, Jan. 1984).*
McCullough, (The Chemistry of Conducting Polythiophenes, Advanced Materials, 10(2), p. 93-116 Jan. 1998).*
Dwivedi et al. ("Electron Donor Acceptor Complexes of Substituted Benzenes with Quinones" Current Science, 51(13) p. 651 Jul. 1982).*
Beaujuge et al. ("Color control in pi-Conjugated Organic Polymers for Use in Electrochromic Devices" Chemical Reviews, 110, 268-320 Jan. 2010).*
Corma, et. al. ("Lewis Acid Cataylsts in Oxidation Reactions: from Homogeneous to Heterogenous Systems" Chemical Reviews, 102, 3837-3892, Oct. 2010).*
Ohno, et al "Novel Catayltic Oxidative Synthesis of Soluble Conductive Polymers of Poly(3-butoxycarbonyl-4-methylpyrrole" Chemistry Letters p. 435-436 28 (5), May 1999).*
Kang et al., Polymerization and Oxidation of Pyrrole by Organic Electron Accepters, Journal of Polymer Science: Polymer Chemistry, 1987, 6 pages.
Machala et al., On-Substrate Polymerization of Solution-Processed, Transparent PEDOT:DDQ Thin Film Electrodes with a Hydrophobic Polymer Matrix, Organic Electronics, May 21, 2011, 5 pages.
Tan et al., Characterization of Organic p/n Junction Photodiodes Based on Poly(Alkylthiophene)/Perylene Diimide Bilayers, Chemistry of Materials, Jun. 1, 2003, 4 pages.
Taniguchi et al., Ring Size Selective Synthesis of Meso-Aryl Expanded Porphyrins, Tetrahedron Letters, 2003, 2 pages.
International Search Report for Application No. PCT/US2012/061179, mail date Jan. 23, 2013, 13 pages.

* cited by examiner

*Primary Examiner* — Randy Gulakowski
*Assistant Examiner* — Christopher M Rodd
(74) *Attorney, Agent, or Firm* — The Marbury Law Group, PLLC

(57) ABSTRACT

An improved polymerization method including a method comprising providing a reaction mixture comprising a first monomer, an organic oxidant, and at least one Lewis acid or Brönsted acid, wherein the first monomer comprises at least one optionally substituted heterocyclic ring, wherein the heterocyclic ring comprises at least one heteroatom; and reacting the reaction mixture to obtain a conjugated polymer. The method can reduce the content of undesirable entities in the polymer such as halogens and metals, which can be useful in organic electronic device applications. Purification methods also are adapted to remove organic and inorganic impurities.

42 Claims, 14 Drawing Sheets

SYNTHESIS OF CONJUGATED POLYMERS VIA OXIDATIVE POLYMERIZATION AND RELATED COMPOSITIONS

RELATED APPLICATIONS

This application claims priority to U.S. provisional application 61/550,322 filed Oct. 21, 2011.

BACKGROUND

As the field of conducting polymers has evolved, it is understood that commercially successful intrinsically conducting polymers (ICPs) require a cost effective synthesis in addition to fine balance of conductivity, processability, and stability. Over the last few years, researchers have utilized synthetic methods and techniques to attempt to control all three properties together. The synthesis of conjugated polymers, including the important polythiophene family of polymers, is usually divided into three polymerization techniques: electrochemical polymerization, oxidative chemical polymerization using metal-based oxidant, and transition metal promoted cross-coupling of organic dihalide groups. For example, the application of these polymerization techniques in the synthesis of polythiophene is described in detail in McCullough, *Adv. Mater.* 10(2):93-116 (1998), which is incorporated herein by reference in its entirety. See also, for example, U.S. Pat. No. 6,166,172 (GRIM polymerization method); U.S. Pat. No. 6,602,974 (block copolymers); and U.S. Pat. No. 7,452,958 (living polymerization). In some embodiments, iodonium salts have been employed for oxidative polymerization of thiophene monomers. (see, for example, Yagci, Y et al, *Macromol. Chem. Phys.* 2005, 206, 1178-1182)

Although these polymerization methods can be useful in the synthesis of conjugated polymers, they still possess a number of limitations, including (a) difficulties in generating large amounts of processable, pure materials; (b) problems in polymerizing many monomers with sensitive/reactive functional groups; and (c) multiple intermediate (synthesis and/or purification) steps in the synthetic route which increases the cost of final products and complicates the development, manufacturing and commercialization processes.

A need exists for improved methods for producing electrically conductive polymers that are fast, reliable, and cost effective.

SUMMARY

Embodiments described herein include, for example, methods for making, compositions, compositions made by particular methods of making, methods of using, devices, and articles.

For example, one embodiment provides a method comprising: polymerizing at least one first monomer in the presence of at least one organic oxidant, wherein the first monomer comprises at least one optionally substituted heterocyclic ring, wherein the heterocyclic ring comprises at least one heteroatom.

For example, in one embodiment, the first monomer consists of one optionally substituted heterocyclic ring. In another embodiment, the first monomer comprises at least two optionally substituted heterocyclic rings. In another embodiment, the first monomer comprises at least three optionally substituted heterocyclic rings. In another embodiment, the first monomer comprises at least two optionally substituted fused heterocyclic rings. In another embodiment, the first monomer comprises at least three optionally substituted fused heterocyclic rings. In another embodiment, the heteroatom is O, S, Se, N, or Si, whereas in another embodiment, the heteroatom is O, S, or N. In another embodiment, the heterocyclic ring is a five-member ring comprising at least one heteroatom, and the heteroatom is S or N. In another embodiment, the heterocyclic ring is a six-member ring comprising at least one heteroatom, and the heteroatom is S or N.

In one embodiment, the first monomer is represented by:

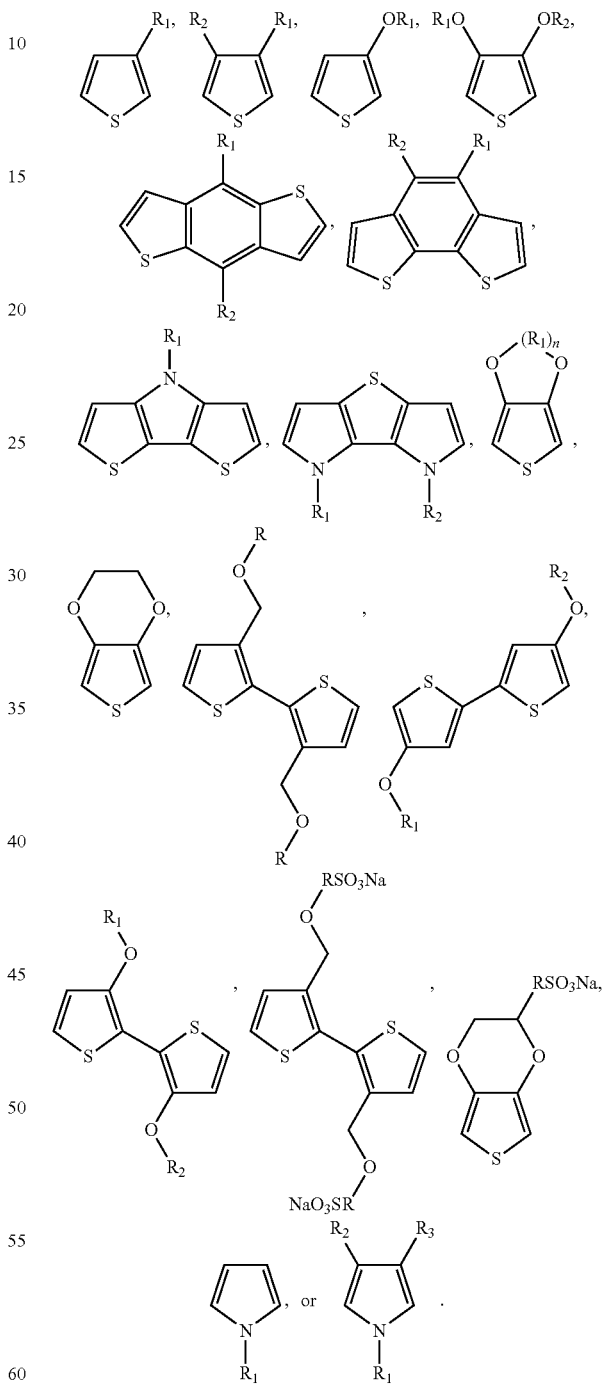

wherein R, $R_1$, $R_2$, and $R_3$ are each a hydrogen or an optionally substituted linear, branched or cyclic alkyl, aryl, alkoxy, aryloxy, alkylthio, arylthio, acyl, ether, or polyether. In another embodiment, R, $R_1$, $R_2$, and $R_3$ comprise a crown ether.

In another embodiment, the first monomer is represented by:

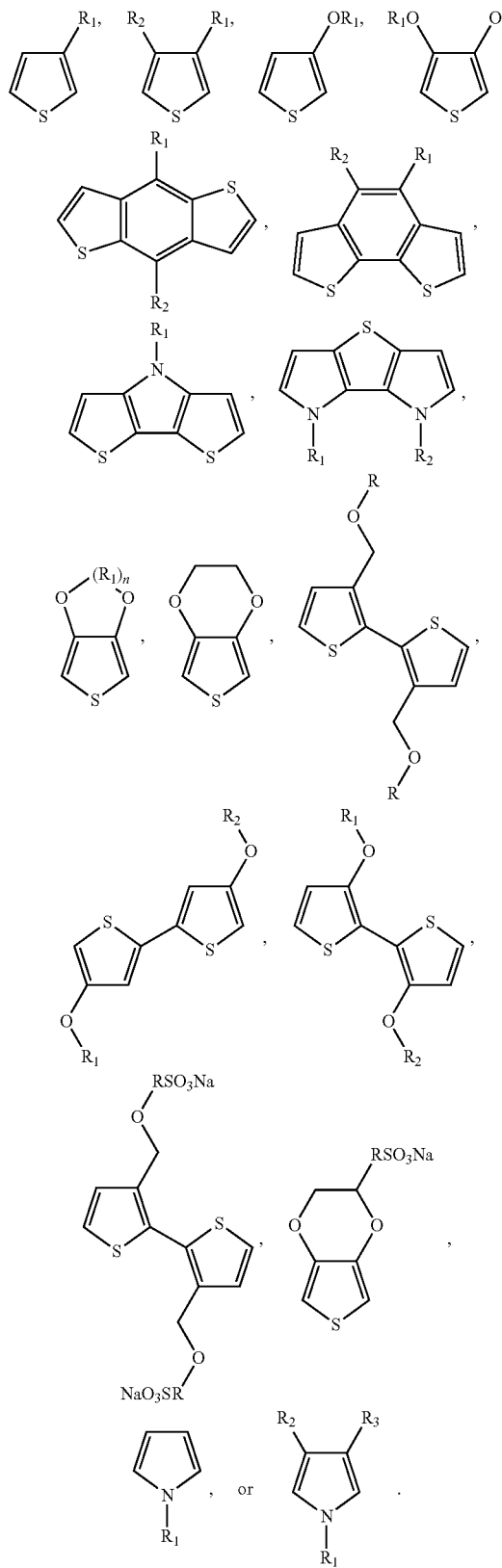

In another embodiment, the first monomer is represented by:

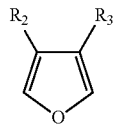

wherein R, $R_1$, $R_2$, and $R_3$ are each independently a linear or branched alkyl, alkoxy, ether or polyether, or together a cyclic alkyl, alkoxy, ether or polyether.

wherein R, $R_1$, $R_2$, and $R_3$ are each a hydrogen or an optionally substituted linear, branched or cyclic alkyl, aryl, alkoxy, aryloxy, alkylthio, arylthio, acyl, ether, or polyether.

In one embodiment, the first monomer is a substituted thiophene. In another embodiment, the first monomer is a 3-substituted thiophene. In another embodiment, the first monomer is a 3,4-substituted thiophene. In another embodiment, the first monomer is a dimer comprising a first optionally substituted thiophene unit and a second optionally substituted thiophene unit.

In other embodiments, the first monomer is free of any halogen substituents. In addition, the first monomer can be free of any polymerizable halogen group directly bonded to the heterocyclic ring.

In one embodiment, the first monomer comprises at least one sulfonate substituent. This can be produced by a sulfonation reaction. In another embodiment, the first monomer comprises at least one fluorinated substituent. In another embodiment, the first monomer comprises at least one polyether substituent. In one embodiment, the first monomer comprises at least one alkoxy substituent. In one embodiment, the organic oxidant comprises an optionally substituted quinone group. In another embodiment, the organic oxidant comprises an optionally substituted quinonimine group or an optionally substituted quinondiimine group. In another embodiment, the organic oxidant comprises an optionally substituted nitroarene group.

In other embodiments, the organic oxidant is represented by formula (I), (II), or (III):

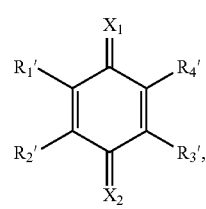 (I)

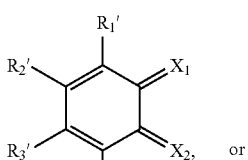 (II)

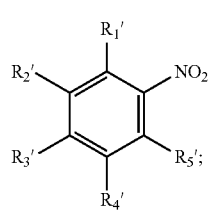 (III)

wherein $X_1$ and $X_2$ are each independently O or N—$R_6'$, and wherein $R_1'$, $R_2'$, $R_3'$, $R_4'$, $R_5'$ and $R_6'$ are each independently a hydrogen, a halogen, or an optionally substituted linear, branched, or cyclic alkyl, alkenyl, alkynyl, alkoxy, alkylthio, ester, ketone, carboxylic acid, carboxylate ester, nitro, sulfonic acid, sulfonate ester, sulfonic acid amide, or cyano group. For example, the organic oxidant can be 2,3-dichloro-5,6-dicyanobenzoquinone (DDQ).

In one embodiment, the polymerizing is carried out with a Lewis acid or Brönsted acid also present.

In another embodiment, the Lewis acid comprises $BF_3$.

In another embodiment, the Lewis acid comprises at least one $BF_3$ etherate.

In another embodiment, the polymerizing is carried out with $BF_3.(C_2H_5)_2O$ present. In another embodiment, the polymerizing is carried out in the presence of at least one solvent. In another embodiment, the polymerizing is carried out substantially in absence of any solvent.

In other embodiments, the reaction mixture further comprises a second monomer different from the first monomer. For example, in one embodiment, the reaction mixture further comprises a second monomer different from the first monomer, wherein the first monomer is 3,4-disubstituted thiophene, and wherein the second monomer is 3-substituted thiophene.

In other embodiments, the method further comprises quenching the reaction with an organometallic quenching agent, a metal quenching agent, or an organic quenching agent. For example, the method can comprise quenching the reaction with at least one metallocene. In another embodiment, the method can comprise quenching the reaction with zinc.

In another embodiment, the method further comprises dedoping the conjugated polymer with at least one reducing agent. For example, the method can further comprise dedoping the conjugated polymer with hydrazine.

In another embodiment, the polymerizing is carried out substantially free of any metal-based oxidant or metal-based catalyst. In another embodiment, the polymerization is carried out without a Brönsted acid. In another embodiment, the polymerization is carried out substantially in absence of any proton source.

Further embodiments comprise one or more compositions comprising a conjugated polymer made by the methods described herein, including the synthesis and purification steps. In one embodiment, the conjugated polymer has an Mw of at least 10,000 or an Mn of at least 5,000. In another embodiment, the conjugated polymer comprises three or more repeating units.

In other embodiments, the conjugated polymer is represented by:

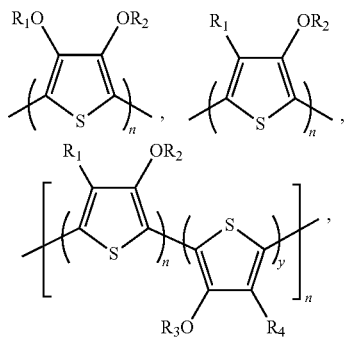

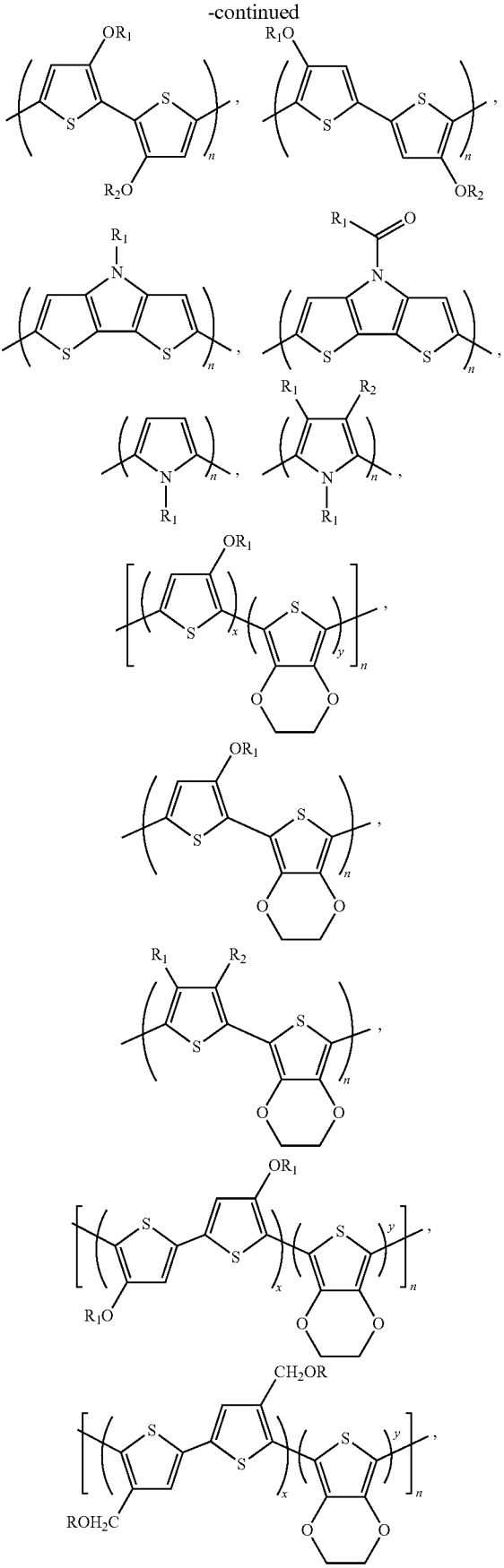

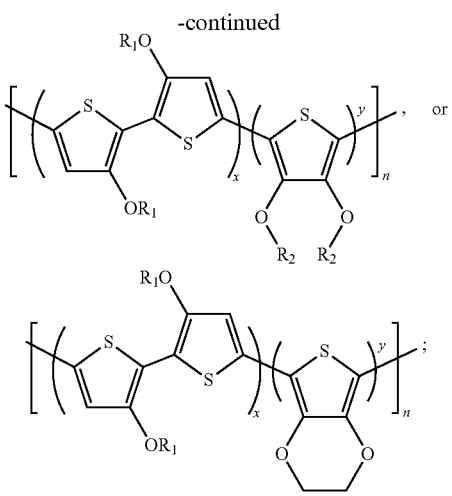

wherein n, x and y are each an integer of one or more; and wherein $R_1$, $R_2$, $R_3$ and $R_4$ are each independently a hydrogen or an optionally substituted linear, branched, or cyclic alkyl, aryl, alkoxy, aryloxy, alkylthio, arylthio, ether, or polyether.

In one embodiment, the conjugated polymer is regioregular. In another embodiment, the conjugated polymer is regio-irregular.

In one embodiment, the conjugated polymer is a homopolymer of 3,4-disubstituted thiophene repeat units. In another embodiment, the conjugated polymer is a copolymer comprising 3,4-disubstituted thiophene repeat units and 3-substituted thiophene repeat units. In other embodiments, the composition has a halogen impurity level of 2,000 ppm or less before de-halogenation. In other embodiments, the composition has a metal impurity level of 1,000 ppm or less before any metal purification step. In other embodiments, the level of organic impurity is less than 10 ppm.

Another embodiment provides a method comprising: polymerizing at least one first monomer in the presence of at least one organic oxidant, wherein the first monomer comprises at least one optionally substituted heterocyclic ring, wherein the heterocyclic ring comprises at least one heteroatom, wherein the first monomer does not comprise a halogen bonded to the heterocyclic ring, and wherein polymerization is carried out without a metal oxidant, initiator, or catalyst.

In one embodiment, the monomer is a thiophene monomer. In another embodiment, the monomer is a 3-substituted thiophene monomer or a 3,4-substituted thiophene monomer. In another embodiment, the organic oxidant is a quinone or a quinone derivative. In another embodiment, the polymerizing step produces a polymer having an Mn of at least 5,000 g/mol. In another embodiment, the polymerizing step is carried out in the presence of a Lewis acid or a Bronsted acid. In another embodiment, the polymerizing step is carried out in the presence of a Lewis acid. In another embodiment, the polymerizing step is carried out in the presence of a Lewis acid and the organic oxidant is a quinone or a quinone derivative. In another embodiment, the method further comprises the steps of treating with a quenching agent and treating with a dedoping reagent. In another embodiment, the polymerizing is carried out with at least one second monomer different from the thiophene monomer.

Another embodiment provides a method comprising: polymerizing at least one first monomer in the presence of at least one organic oxidant and at least one acid. In one embodiment, the monomer comprises at least one heterocyclic thiophene ring. In another embodiment, the acid is a Lewis acid or a Brönsted acid. In another embodiment, the organic oxidant is a quinone or quinone derivative. The organic oxidant can be, for example, DDQ. In another embodiment, the polymerization produces a polymer, and the polymer is purified so the level of organic oxidant is less than 1,000 ppm. In another embodiment, the polymerization produces a polymer, and the polymer is purified so the level of organic oxidant is less than 10 ppm. In another embodiment, the polymerization produces a polymer, and the polymerizing is quenched with zinc. In another embodiment, the polymerization produces a polymer, and the polymerizing is quenched with zinc and the polymer is washed with methanol. In another embodiment, the monomer comprises a ring and does not comprise a halogen atom bonded to the ring.

Another embodiment provides a method comprising: (i) providing a reaction mixture comprising at least one first monomer, at least one organic oxidant, and at least one Lewis acid or Brönsted acid, wherein the first monomer comprises at least one optionally substituted heterocyclic ring, wherein the heterocyclic ring comprises at least one heteroatom; (ii) polymerizing the monomer to form a conjugated polymer; (iii) quenching the reaction with a quenching agent, and (iv) dedoping the conjugated polymer. In one embodiment, the quenching reagent is zinc. In another embodiment, the conjugated polymer is washed with methanol. In another embodiment, the conjugated polymer is washed with a mixture of at least one alcohol and aqueous acid and/or a mixture of reducing agent and water. In another embodiment, the organic oxidant is DDQ and the level of DDQ after purification is less than 1,000 ppm. In another embodiment, the organic oxidant is DDQ and the level of DDQ after purification is less than 10 ppm.

Another embodiment provides a method comprising: oxidatively polymerizing at least one first monomer comprising at least one heterocyclic ring, wherein the polymerization is carried out substantially in absence of any solvent. In one embodiment, the first monomer comprises at least one optionally substituted thiophene ring, and wherein the polymerization is carried out in the presence of at least one the organic oxidant and at least one Lewis acid. In another embodiment, the polymerization results in a polymer composition having a halogen impurity level of 2,000 ppm or less and a metal impurity level of 1,000 ppm or less.

Another embodiment provides for a method comprising: oxidatively polymerizing at least one first monomer comprising at least one heterocyclic ring, wherein the polymerization is carried out substantially in absence of any proton source. In one embodiment, the first monomer comprises at least one optionally substituted thiophene ring, and wherein the polymerization is carried out in the presence of at least one the organic oxidant and at least one Lewis acid. In another embodiment, the polymerization results in a polymer composition having a halogen impurity level of 2,000 ppm or less and a metal impurity level of 1,000 ppm or less.

Another embodiment provides a method comprising: oxidatively polymerizing at least one first monomer comprising at least one heterocyclic ring, wherein the polymerization is carried out without a metal oxidant, metal initiator or metal catalyst, and wherein the first monomer is not treated with any halogenation step before polymerization. In one embodiment, the first monomer comprises at least one optionally substituted thiophene ring, and wherein the polymerization is carried out in the presence of at least one the organic oxidant and at least one Lewis acid.

Another embodiment provides a conjugated copolymer, optionally prepared by the methods described herein, comprising:

(i) at least one first repeat unit represented by:

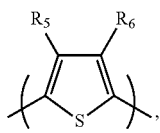

wherein $R_5$ and $R_6$ are each independently an optionally substituted linear, branched, or cyclic alkoxy, alkylene oxide or polyether, or together form a ring; and
(ii) at least one second repeat unit represented by

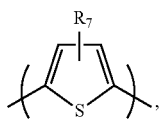

wherein $R_7$ is an optionally substituted linear, branched, or cyclic alkyl, alkoxy, alkylene oxide or polyether. In one embodiment, the first repeating unit is 3,4-dipolyether-thiophene or 3,4-ethylenedioxy-thiophene. In another embodiment, the second repeat unit is 3-alkyl-thiophene, 3-polyether-thiophene, or 3-(2,2,2-trifluoroethoxy)thiophene.

In one embodiment, the conjugated polymer has an Mn of at least 1,000. In another embodiment, the polymerizing step produces a polymer having an Mn of at least 1,000 g/mol.

In another embodiment, the first monomer is represented by:

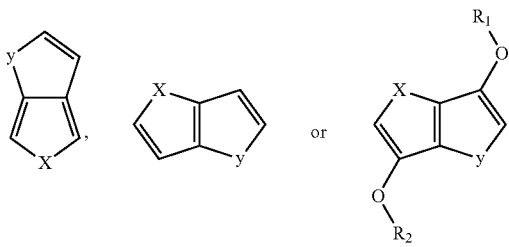

wherein x and y are independently represented by NR, O, S, or Se, and wherein $R_1$ and $R_2$ are each a hydrogen or an optionally substituted linear, branched or cyclic alkyl, aryl, alkoxy, aryloxy, alkylthio, arylthio, acyl, ether, or polyether.

A variety of advantages can be found for at least one embodiment. For example, at least one advantage for at least one embodiment includes better purity of polymers including, for example, halogen and metal content. Side reactions can be minimized or eliminated.

At least one additional advantage for at least one embodiment includes cost effectiveness.

At least one additional advantage for at least one embodiment includes the absence of any halogenation step which affords stable and highly pure monomeric precursors.

At least one additional advantage for at least one embodiment includes the absence of any functional end groups such as boronic acids for Suzuki reaction or —$SnR_3$ for Stille reaction.

At least one additional advantage for at least one embodiment includes the absence of any dehalogenation step and/or end-capping step to remove functional groups such as halogen, methylated tin, and the like.

At least one additional advantage for at least one embodiment is that regioregularity can be controlled for un-symmetric monomers via, for example, choice of organic oxidant, choice of Lewis acid, rate of addition of oxidant, and concentration. Additional advantages for at least some embodiments include the absence of any dehalogenation step of polymer that requires additional organometallic reagents and/or metal-based catalysts, e.g., Grignard or organolithium reagents and Ni(0) or Pd(0), respectively. It has been known in the art that presence of halogens and/or metals can reduce lifetime of organic electronic devices. Thus, reducing and/or avoiding using these reagents during polymerizations can (1) reduce labor and number of synthetic steps, and/or (2) expedite and improve manufacturing process.

DETAILED DESCRIPTION

Introduction

Figure 1A:
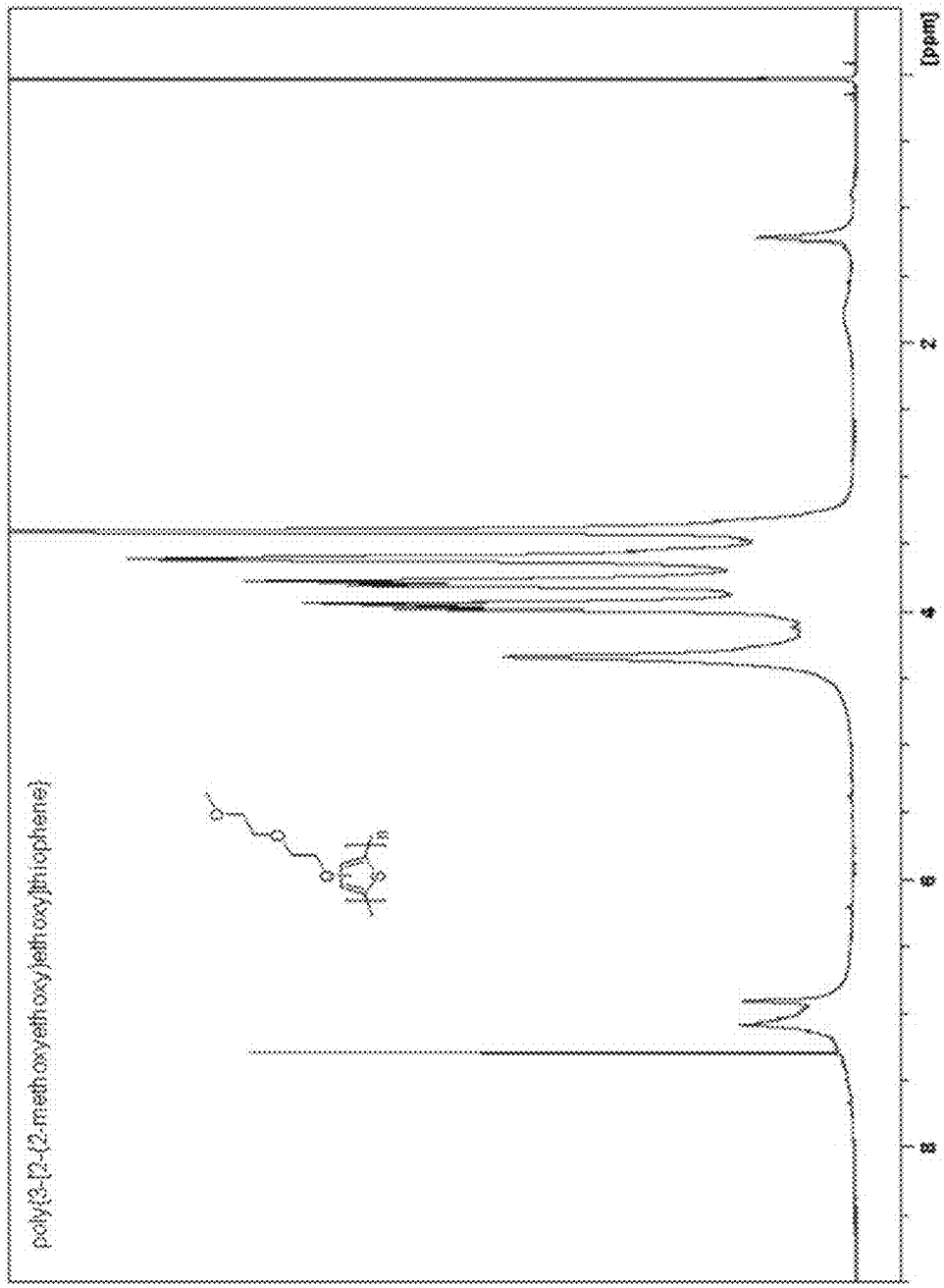
FIG. 1a shows $^1$H NMR (500 MHz) spectra of poly{3-[2-(2-methoxyethoxy)ethoxy]thiophene} (PMEET) synthesized via oxidative method.

Priority application U.S. provisional application 61/550,322 filed Oct. 21, 2011 is hereby incorporated by reference in its entirety.

Provided herein are embodiments, as claimed, for an oxidative chemical polymerization utilizing organic oxidants for the synthesis of conjugated polymers with low oxidation potentials. This type of oxidative polymerization present multiple advantages in contrast to other common oxidative polymerizations, which utilize metal based oxidants, e.g., ferric chloride ($FeCl_3$), and are complicated by the removal of residual metal ions which, in turn, can prevent the complete reduction of the easily oxidized polymers. Furthermore, oxidative chemical polymerization with $FeCl_3$ can produce molecular weight fractions of these polymers that are infusible and insoluble solids due to cross-linking via $\alpha,\beta'$ couplings between thiophene rings. [Chen, S. An.; Tsai, C. C. *Macromolecules*, 1993, 26, 2234].

All references described herein are hereby incorporated by reference in their entirety.

Various terms are further described herein below:

"A", "an", and "the" refers to "at least one" or "one or more" unless specified otherwise.

"Optionally substituted" groups can be, for example, functional groups that may be substituted or unsubstituted by additional functional groups. For example, when a group is unsubstituted by an additional group it can be referred to as the group name, for example alkyl or aryl. When a group is substituted with additional functional groups it may more generically be referred to as substituted alkyl or substituted aryl.

"Heterocyclic ring" can be, for example, a carbocyclic ring wherein at least one carbon atom is substituted with a heteroatom. The heteroatom can be, for example, O, S, N, P, etc. Preferred heterocyclic rings include five-member ring and six-member ring "Alkyl" can be, for example, straight chain or branched alkyl groups having from 1 to 20 carbon atoms, or from 1 to 15 carbon atoms, or from 1 to 10, or from 1 to 5, or from 1 to 3 carbon atoms. This term is exemplified by groups such as for example methyl, ethyl, n-propyl, iso-propyl, n-butyl, t-butyl, n-pentyl, ethylhexyl, dodecyl, isopentyl, and the like.

"Aryl" can be, for example, an aromatic carbocyclic group of from 5 to 14 carbon atoms having a single ring (e.g., phenyl) or multiple condensed rings (e.g., naphthyl or anthryl) which condensed rings may or may not be aromatic provided that the point of attachment is at an aromatic carbon atom. Preferred aryls include phenyl, naphthyl, and the like.

"Alkoxy" can be, for example, the group "alkyl-O—" which includes, by way of example, methoxy, ethoxy, n-propyloxy, iso-propyloxy, n-butyloxy, t-butyloxy, n-pentyloxy, 1-ethylhex-1-yloxy, dodecyloxy, isopentyloxy, and the like.

"Aryloxy" can be, for example, the group "aryl-O—" which includes, by way of example, phenoxy, naphthoxy, and the like.

"Thioalkyl" can be, for example, the group "alkyl-S-" which includes, by way of example, thiomethyl, thioethyl, and the like.

"Thioaryl" can be, for example, the group "aryl-S-" which includes, by way of example, thiophenyl, thionaphthyl, and the like.

"Acyl" can be, for example, the groups "H/alkyl/aryl-C(O)-", wherein the alkyl and aryl group can be optionally substituted.

"Ether" can be, for example, the group "alkyl/aryl-O-alkylene/arylene-", wherein the alkyl, aryl, alkylene and arylene group can be optionally substituted.

"Polyether" can be, for example, the group "H/alkyl/aryl-(alkylene-O)$_n$-" or the group "H/alkyl/aryl-(O-alkylene)$_n$-", wherein the alkyl, aryl, alkylene and arylene group can be optionally substituted.

"Ester" can be, for example, the group "alkyl/aryl-C(O)—O-alkylene/arylene-", wherein the alkyl, aryl, alkylene and arylene group can be optionally substituted.

"Ketone" can be, for example, the group "alkyl/aryl-C(O)-alkylene/arylene-", wherein the alkyl, aryl, alkylene and arylene group can be optionally substituted.

First Monomer

Embodiments described herein relate to a conjugated polymer obtained by polymerizing at least one first monomer. A polymer can be prepared which is a homopolymer or a copolymer. The polymer can comprise, for example, at least 50, or at least 60, or at least 70, or at least 80, or at least 90, or at least 95, or at least 99 molar percent of repeat units based on the first monomer.

The first monomer can be, for example, an organic compound comprising at least one optionally substituted heterocyclic ring. The heterocyclic ring can comprise, for example, at least one heteroatom, or at least two heteroatoms, or at least three heteroatoms. The heteroatom can be, for example, O, S, or N. The heteroatom also can be Si. The heterocyclic ring can be, for example, a five member ring comprising at least one of S and N, or a six-member ring comprises at least one of S and N.

Moreover, the first monomer, can comprises, for example, two or more optionally substituted heterocyclic rings, or three or more optionally substituted heterocyclic rings, or four or more optionally substituted heterocyclic rings, or a combination of one or more heterocyclic rings and one or more carbocyclic rings.

Furthermore, the heterocyclic rings and the optional carbocyclic rings can be saturated or unsaturated. The heterocyclic rings and the optional carbocyclic rings can be substituted or unsubstituted. For example, at least one heterocyclic ring can be substituted with at least one optionally substituted alkyl, alkoxy, alkylthio, aryl, aryloxy, arylthio, acyl, ether, or polyether group. The substituent group can be linear, branched or cyclic.

Still, further, the heterocyclic rings and the optional carbocyclic rings can be, for example, fused together or connected via covalent aryl-aryl bond. Accordingly, the first monomer can comprises, for example, at least two optionally substituted heterocyclic rings connected by covalent aryl-aryl bond, or at least three optionally substituted heterocyclic rings connected by covalent aryl-aryl bond, or at least two optionally substituted heterocyclic rings fused together, or at least three optionally substituted heterocyclic rings fused together.

The first monomer can be also an oligomer such as a dimer or trimer. For example, coupling reactions can be carried out wherein a low molecular weight oligomer is first prepared and then subjected to polymerization. An example of this approach can be found in for example US Patent Publication No. 2011/0251370.

The first monomer can comprise a non-heterocyclic bridge. For example, the monomer can be represented by H1-A-H2 wherein H1 and H2 are heterocyclic moieties but A is a non-heterocyclic bridging moiety such as, for example, phenyl, biphenyl, or fluorene.

In one embodiment, the first monomer is an optionally substituted thiophene, pyrrole, or dithieno[3,2-b:2',3'-d]pyrrole.

The substituents which form side groups are not particularly limited. In general, they can be substituents which allow for an oxidative polymerization without degradation. They can provide a solubilizing function. Examples include hydrogen, alkyl, fluoroalkyl (including perfluoroalkyl and partially fluorinated alkyl), alkoxy optionally substituted with at least one fluoroalkyl group, and polyether optionally substituted with at least one fluoroalkyl group. Silicon substituents can be used such as, for example, —Si(R)$_3$, wherein R is an organic group such as alkyl or alkoxy. Two substituents can join to form a ring structure.

Examples of the first monomer include the following:

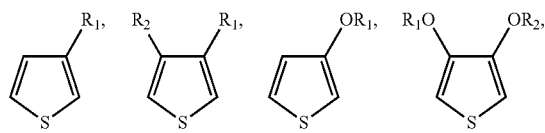

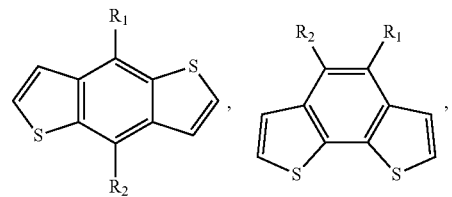

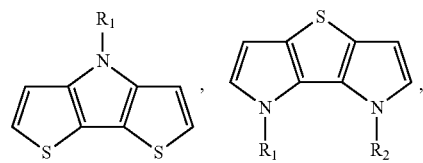

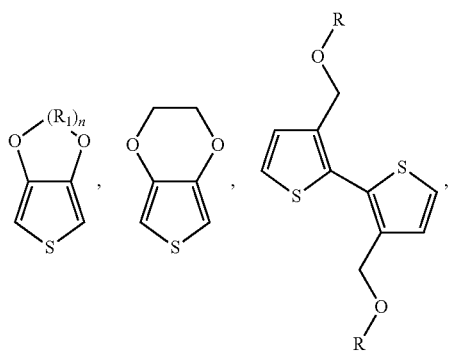

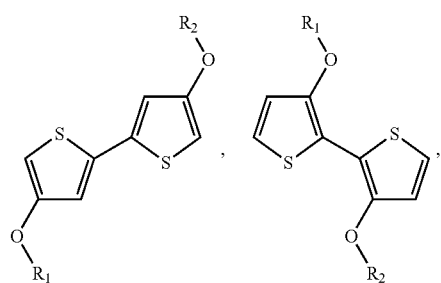

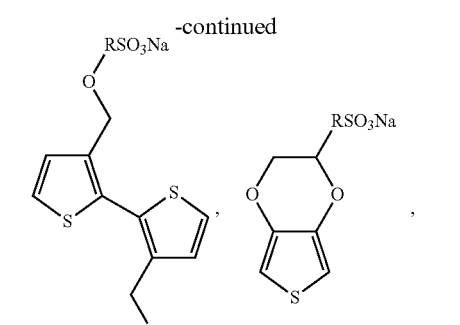

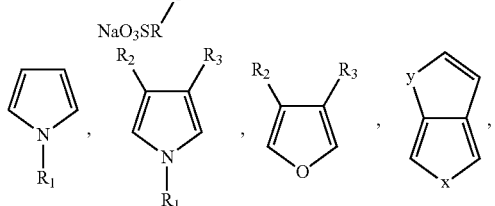

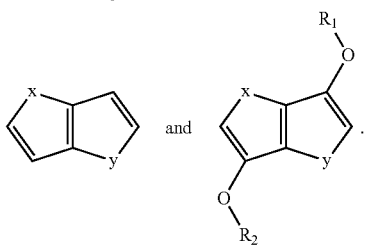

wherein substituents R, $R_1$, $R_2$, and $R_3$ are each independently a hydrogen or an optionally substituted linear, branched, or cyclic alkyl, aryl, alkoxy, aryloxy, alkylthio, arylthio, acyl, ether, or polyether. The substituent can also comprise one or more halogen moieties such as fluoro, chloro, bromo, or iodo. R, $R_1$, $R_2$, and $R_3$ can be, for example, fluoroalkyl, or alkoxy or polyether optionally substituted with at least one fluoroalkyl. Perfluorinated groups can be used. The substituent can also comprise one or more ionic moieties such as sulfonate or carboxylic including acid, salt, and basic forms. For example, one can prepare water soluble polymers. X and Y are independently selected from NR, O, S, or Se.

Substituents can be electron-withdrawing or electron-releasing moieties. They can be polar or non-polar groups.

In some embodiments, the first monomer is a substituted thiophene. In some embodiment, the first monomer is substantially free of any halogen substitution, such as less than 5 wt. % of halogen, or less than 2 wt. % of halogen, or less than 1 wt. % of halogen, or less than 0.5 wt. % of halogen, or less than 0.2 wt. % of halogen, or less than 0.1 wt. % of halogen. In one embodiment, the first monomer comprises a 3-substituted thiophene which comprises halogen in the 3-substituent but free of any halogen at 2 and 5 positions. In another embodiment, the first monomer comprises a 3,4-disubstituted thiophene which comprises halogen in the 3-substituent and/or the 4-substituent but free of any halogen at 2 and 5 positions.

In some embodiment, the first monomer is substantially free of any halogen group directly bonded to the heterocyclic ring of the first monomer; however, the first polymer may comprises, for example, a fluorinated or brominated side chain, or at least one non-polymerizable fluorine directly bonded to the heterocyclic ring of the first monomer.

Examples of monomers can be found in, for example, US Patent Publications 2006/0078761 and 2009/0256117 and U.S. Pat. Nos. 7,569,159 and 8,017,241.

Bithiophene monomers can be used. See, for example, Zagorska, *Polymer,* 1990, 31, July, 1379; Fald et al., *Macromolecules,* 1993, 26, 2501-2507.

Polymers can be self-doped. For example, ionic groups like sulfonate can be linked directly to the monomer and polymer. See, e.g., Karlsson et al., *Chem. Mater.,* 2009, 21, 1815-1821.

In one embodiment, the monomer is a symmetric monomer. In another embodiment, the monomer is an unsymmetric monomer.

Thiophene, pyrrole, and aniline polymerization, as well as oxidative polymerization, is described in, for example, Percec and Hill, Chapter 7, "Step-Growth Electrophilic Oligomerization and Polymerization Reactions," pgs. 555-682 in *Cationic Polymerization: Mechanisms, Synthesis, and Applications*, Matyjaszewski (ed.), 1996.

Oxidant

The oxidant can be an organic oxidant, and organic oxidants are known in the art and described in, for example, U.S. Pat. No. 7,368,624, which is incorporated herein by reference in its entirety. Organic oxidants suitable for the polymerization reaction described herein include, for example, optionally substituted quinones, optionally substituted quinone derivatives such as quinone imines and quinone diimines, and optionally substituted nitroarenes.

In some embodiments, the organic oxidants are represented by formulas I, II or III:

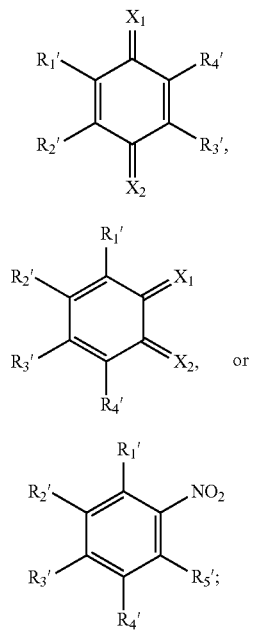

wherein $X_1$ and $X_2$ are each O or N—$R_6'$, and wherein $R_1'$, $R_2'$, $R_3'$, $R_4'$, $R_5'$ and $R_6'$ can be, for example, a hydrogen, a halogen, or an optionally substituted linear, branched, or cyclic alkyl, alkenyl, alkynyl, alkoxy, alkylthio, ester, ketone, carboxylic acid, carboxylate ester, nitro, sulfonic acid, sulfonate ester, sulfonic acid amide, or cyano. The groups may also be incorporated into a ring system, for example to form polyaromatic quinones or polyaromatic quinone diimines such as 1,4-naphthoquinone, or to form polyaromatic nitroarenes such as nitronaphthalenes.

In some embodiments, the organic oxidant is a quinone or quinone derivative selected from the following:

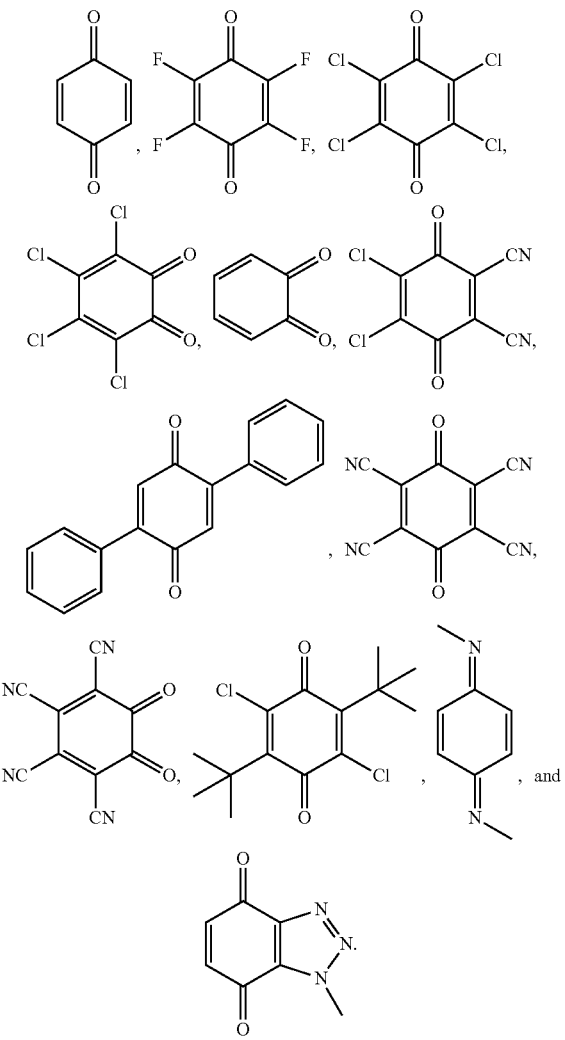

In some embodiments, the organic oxidant is a optionally substituted nitroarenes selected from the following:

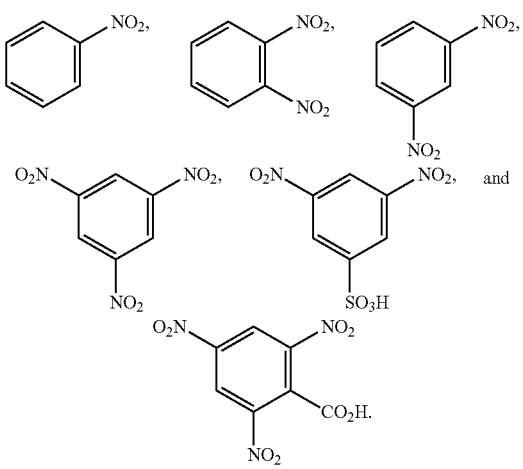

In one embodiment, the organic oxidant is 2,3-dichloro-5,6-dicyanobenzoquinone (DDQ).

In some embodiments, metal-based oxidants such as iron trichloride can be excluded. The organic oxidant can be free of metal. For example, iron trichloride oxidant, in contrast, might complex or π-bond to aromatic polymers and be difficult to remove (see, for example, Work, et al, *Inorganic Chemistry*, 12, 8, 1973, 1936-1938). In one embodiment, iron trichloride and other metal-based oxidants are excluded totally. In another embodiment, the reaction mixture does not comprise $Br_2$ as oxidant.

In one embodiment, the organic oxidant is not a salt, and in other embodiments, is not an iodonium salt.

Lewis Acid and/or Bronsted Acid

Lewis acids and Brönsted acids are known in the art and are described in, for example, U.S. Pat. No. 7,368,624 and R. P. Bell, *The Proton in Chemistry*, second edition, Cornell University Press, Ithaca, N.Y. 1973, both of which are incorporated herein by reference in their entireties. Brönsted acids are generally proton donors while Lewis acids are more broadly defined as compounds containing a vacant orbital which can accept an unshared pair of electrons from a base.

In one embodiment, a Lewis acid is used exclusively as the acid. In one embodiment, the Brönsted acid is not used. The Brönsted acid can be excluded. In a preferred embodiment, the reaction mixture is substantially or totally free of any proton source to avoid unwanted side reactions.

In one embodiment, the Brönsted acid is a trichloroacetic acid, a trifluoroacetic acid, a trifluoromethanesulfonic acid, a methanesulfonic acid, a fluorosulfonic acid, and/or a hexafluoroisopropanol. The Brönsted acids may also be used in combination, such as a combination of trifluoroacetic acid and methanesulfonic acid.

Examples of the Brönsted acid include the following: $CF_3SO_3H$, $C_6H_5SO_3H$, $CH_3SO_3H$, $CF_3CO_2H$, $CCl_3CO_2H$, $CHCl_2CO_2H$, $CFH_2CO_2H$, $CClCH_2CO_2H$, $HCO_2H$, $C_6H_5CO_2H$, $CH_3CO_2H$, $HBF_4$, $H_2SO_4$, $FSO_3H$, and $HPF_6$.

In one embodiment, trifluoroacetic acid is excluded.

The Lewis acid described herein include any species that is capable of accepting an electron-pair (IUPAC Compendium of Chemical Terminology, The Gold Book, Second Ed., A. D. McNaught and A. Wilkinson, Blackwell Science, 1997).

In one embodiment, the Lewis acid are based on metals from Groups, IIA, IIB, IIIA, IIIB, IVB, WA, VA, VB, VIB and VIIB of the Periodic Table of the Elements. Among them, the Group IIB Lewis acids can be represented by, for example, formula (IV): $MX_2$ (IV), wherein M is a Group IIB metal, X is a halogen or an organic ligand.

The Group IIIA and IIIB Lewis acid can be represented by, for example, formula (V): $R_nMX_{(3-n)}$ (V), wherein n is equal to 1 or 2, each R is either the same or different aryl or alkyl C1 to C15 linear or cyclic group, and each X is the same or different halogen; and wherein M is a Group IIIA or IIIB metal.

The Group IVB and WA Lewis acid can be represented by, for example, formula (VI): $MX_4$ (VI) wherein M is a Group IVB metal, X is a ligand such as halogen. Examples include titanium tetrachloride, zirconium tetrachloride, or tin tetrachloride.

The Group VB and VA Lewis acid can be represented by, for example, formula (VII): $MX_y$ (VII) wherein M is a Group V metal, X is a ligand such as halogen, and y is an integer from 3 to 5. Examples include vanadium tetrachloride and antimony pentafluoride.

In one embodiment, the Lewis acid comprise an element from rows I-V of the Periodic Table. In another embodiment, the Lewis acid comprises an element from rows I-IV of the Periodic Table. In a further embodiment, the Lewis acid comprises an element from rows I-III of the Periodic Table.

In one embodiment, the Lewis acid comprises an element from group IIA-VIIB or IIB-VA of the Periodic Table. In another embodiment, the Lewis acid comprises an element from group IIA-IIIB or IIIA-IVA of the Periodic Table. In a further embodiment, the Lewis acid comprises an element from group IVB or IIIAA of the Periodic Table.

In one embodiment, the Lewis acid comprises a compound of B, Al, Ti, Zr, Sn, Sb, Sc, La, or Zn. In another embodiment, the Lewis acid comprises a halogen or an organic ligand. In a further embodiment, the Lewis acid comprises a halogen such as F or Cl. In yet another embodiment, the Lewis acid comprises an organic ligand selected from $CF_3SO_3^-$, $CH_3CO_2^-$, and $NO_3^-$.

Examples of the Lewis acid include the following: $BF_3$, $BF_3.(C_2H_5)_2O$, $BCl_3$, $BBr_3$, $AlCl_3$, $Al(CH_3)_3$, $TiCl_4$, $ZrCl_4$, $SnCl_4$, $SnCl_4.5H_2O$, $SnF_4$, $VCl_4$, $SbF_5$, $ScCl_3$, $ScCl_3.6H_2O$, $Sc(CF_3SO_3)_3$, $La(CH_3CO_2).xH_2O$, $LaCl_3$, $LaCl_3.7H_2O$, $LaF_3$, $La(NO_3)_3.6H_2O$, $La(C_2O_4)_3.xH_2O$, $La(SO_4)_3.xH_2O$, $La(CF_3SO_3)_3$, $ZnCl_2$, $ZnBr_2$, $ZnF_2$, $Zn(CH_3CO_2)_2$, $Zn(CH_3CO_2)_2.2H_2O$, $ZnSiF_6.xH_2O$, $Zn(NO_3)_2.xH_2O$, $Zn(C_2O_4)_2.xH_2O$, and $Nd(CF_3SO_3)_3$.

In one embodiment, the Lewis acid is $BF_3.(C_2H_5)_2O$. In another embodiment, a combination of Lewis acid and Brönsted acid is used, such as a combination of $CF_3CO_2H$ and $BF_3.(C_2H_5)_2O$.

A Lewis acid can be used in adduct form such as an adduct with diethylether or dimethylsulfide.

Quenching Agent

Polymerization can be stopped by use of a quenching agent, which is either added directly to the reaction mixture or is contacted with the polymer as part of purification and work-up. Quenching agents are known in the art and described in, for example, U.S. Pat. No. 7,368,624 and *Oxidizing and Reducing Agents; Handbook of Reagents for Organic Synthesis*, S. D. Burke and R. L. Danheiser, Wiley, 1999, both of which are incorporated herein by reference in their entireties. The quenching agent can be used to terminate the reaction, which can improve the purity and yield of the desired product.

In one embodiment, the quenching agent is an organometallic quenching agent. Organometallic quenching agent include, for example, metallocenes, such as ferrocene and zirconocene, metal cyanides hexacyanoferrate and hexacyanoruthenate.

In another embodiment, the quenching agent is an organic quenching agent. Organic quenching agents include, for example, aliphatic and aromatic amines, alcohols, aromatic ethers, and heterocycles containing nitrogen and/or sulfur.

In a further embodiment, the quenching agent is an inorganic quenching agent. Inorganic quenching agent can include, for example, Li, Na, K, Zn, Mg, Co, Fe, Al, Sn and their complexes such as $FeCl_2$ and $SnCl_2$. Also, the quenching agent can be a metal quenching agent including zinc.

Preferably, the quenching agents are those that are commercially available and inexpensive, soluble in the reaction medium, and readily separable from the reaction product mixture. However, in some embodiments, metals are not preferred because they introduce additional risks such as fire and purification challenges.

Examples of the quenching agents include the following: metallocenes such as ferrocene, zirconocene,

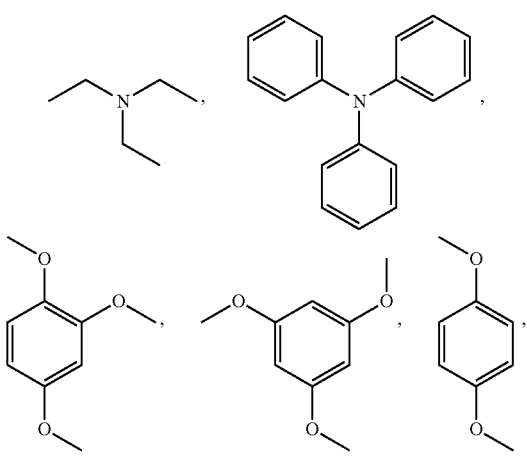

and methanol.

In one embodiment, the quenching agent is ferrocene. In one embodiment, the quenching agent is not methanol.

Quenching agents are preferred which are easily removed and/or do not cause undesired functionality to appear on the polymer.

Polymerization of First Monomer

Many embodiments described herein relate to the polymerization of the first monomer, with or without other monomers, and polymerizing is known in the art. The polymerization reaction can comprise, for example, the following steps: (i) providing a reaction mixture comprising a first monomer, an organic oxidant, and at least one Lewis acid and/or Brönsted acid, wherein the first monomer comprises at least one optionally substituted heterocyclic ring, wherein the heterocyclic ring comprises at least one heteroatom; and (ii) reacting the reaction mixture to form a conjugated polymer.

Optionally, the polymerization reaction also comprises one or more of the following steps: (iii) quenching the reaction with a quenching agent, and (iv) dedoping (reducing) the conjugated polymer. Materials suitable for dedoping the conjugated polymer include, for example, a reducing agent such as hydrazine. Other examples include bases, ammonia, ammonium hydroxide, hydroxylamine, and its derivatives, tetrabutylammonium hydroxide.

In addition to the first monomer, the organic oxidant and the Lewis acid and/or Brönsted acid, the reaction mixture can also comprise, for example, one or more solvents including mixtures of solvents. Solvents suitable for the polymerization reaction described herein include, for example, an organic solvent such as, for example, a halogenated solvent such as, for example, CHCl$_3$ or dichloromethane. In some embodiments, the solvent includes a fluorinated ether, such as trifluoromethyl ether. In other embodiments, the solvent includes an high boiling ether such as dibutyl ether. Non-halogenated solvents can be also used. Additional solvents include, for example, acetonitrile, methanol, and mixtures of thereof, or water.

In addition, the reaction mixture can also comprise at least one second monomer structurally different from the first monomer. Examples include 3,4-ethylenedioxythiophene (EDOT), thiophene, pyrrole, benzobithiophene, carbazoles, fluorenes, and derivatives of thereof.

The reaction mixture can be, for example, substantially or totally free of any solvent other than the monomers. For example, the reaction mixture can consist essentially of the first monomer, the organic oxidant, the Lewis acid/Brönsted acid, and optionally one or more additional monomers. Further, the reaction mixture can consist of the first monomer, the organic oxidant, the Lewis acid/Brönsted acid, and optionally one or more additional monomers. The amount of solvent can be, for example, less than 20 wt. % of the reaction mixture, or less than 10 wt. % of the reaction mixture, or less than 5 wt. % of the reaction mixture, or less than 2 wt. % of the reaction mixture, or less than 1 wt. % of the reaction mixture. Further, the solvent-free reaction mixture can be, for example, substantially or totally free of any metal-based oxidant or Br$_2$ oxidant.

The overall synthesis of monomer and polymer can be, for example, free of any monomer halogenation step. The overall synthesis of monomer and polymer can be, for example, free of any polymer de-halogenation step.

The reaction mixture can be, for example, free of any metal-based oxidants or metal-based catalysts. The reaction mixture can be, for example, substantially free of metal ions, such as less than 1 wt. % of metal ions, or less than 0.5 wt. % of metal ions, or less than 0.2 wt. % of metal ions, or less than 0.1 wt. % of metal ions, or less than 0.05 wt. % of metal ions, or less than 0.02 wt. % of metal ions, or less than 0.01 wt. % of metal ions.

The reacting step (ii) can be conducted at a temperature of, for example, less than 200° C., or less than 150° C., or less than 100° C., or less than 50° C., or less than 25° C. Polymerization can be carried out at, for example, 50° C. to 150° C., or 70° C. to 120° C., or 10° C. to 80° C., or 18° C. to 25° C.

The reacting step (ii) can be conducted for a time period of, for example, 2 hours or more, or 4 hours or more, or 8 hours or more, or 12 hours or more, or 24 hours or more, or 48 hours or more. Polymerization can be carried out for, for example, 2 to 96 hours, or 4 to 48 hours, or 6 to 24 hours.

The molar ratio of the first monomer to the organic oxidant can be, for example, 1:8 or less, or 1:4 or less, or 1:2 or less, or 1:1 to 1:8, or 1:2 to 1:4.

The molar ratio of the first monomer to the Lewis/Brönsted acid can be, for example, 10:1 or more, or 4:1 or more, or 2:1 or more, or 1:2 or more, or 1:4 or more, or 2:1 to 1:8, or 1:1 to 1:4.

Representative polymerizations are shown below, including un-symmetrical and symmetrical thiophene monomers:

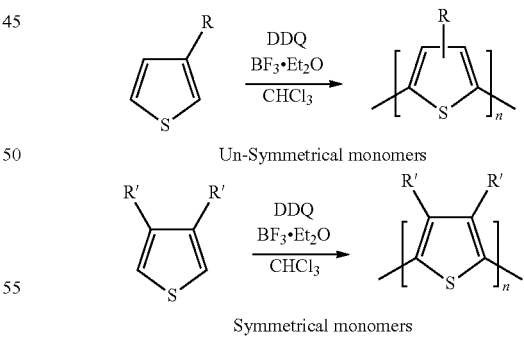

Un-Symmetrical monomers

Symmetrical monomers wherein each R' is the same.

Conjugated Polymer

Many embodiments described herein relate to composition comprising a conjugated polymer obtained by polymerizing the first monomer, with or without other monomers. Copolymerization can be carried out. The conjugated polymer can be, for example, soluble in at least one common inorganic or organic solvent such as chlorobenzene. The Mw of the polymer can be, for example, 10,000 or more, or 15,000 or more, or 20,000 or more, or 25,000 or more, or 30,000 or more, or 50,000 or more, or 100,000 or more. The Mn of the polymer can be, for example, 1,000 or more, or 2,000 or more, or 3,000 or more, or 4,000 or more, or 5,000 or more, or 10,000 or more, or 15,000 or more, or 20,000 or more, or 30,000 or more, or 50,000 or more. The average number of repeat units can be, for example, at least 40, or at least 50, or at least 100.

In some embodiments, the conjugated polymer comprises three or repeating units, which can be same or different. In one embodiment, the conjugated polymer is an oligomer comprises at least one 3,4-ethylenedioxythiophene comonomer. In one embodiment, the conjugated polymer is a trimer or tetramer.

The composition comprising the conjugated polymer can be, for example, substantially free of any halogen ions, such as less than 1 wt. % of halogen ions, or less than 0.5 wt. % of halogen ions, or less than 0.2 wt. % of halogen ions, or less than 0.1 wt. % of halogen ions, or less than 0.05 wt. % of halogen ions, or less than 0.02 wt. % of halogen ions, or less than 0.01 wt. % of halogen ions, or less than 0.001 wt. % of halogen ions. The halogen impurity level before de-halogenation can be, for example, less than 5,000 ppm, or less than 2,000 ppm, or less than 1,000 ppm, or less than 500 ppm, or less than 200 ppm, or less than 100 ppm, or less than 50 ppm.

The composition comprising the conjugated polymer can be, for example, substantially free of residual metal, such as less than 1 wt. % of residual metal, or less than 0.5 wt. % of residual metal, or less than 0.2 wt. % of residual metal, or less than 0.1 wt. % of residual metal, or less than 0.05 wt. % of residual metal, or less than 0.02 wt. % of residual metal, or less than 0.01 wt. % of residual metal, or less than 0.001 wt. % of residual metal. The metal impurity level before any metal purification step can be, for example, less than 1,000 ppm, or less than 500 ppm, or less than 200 ppm, or less than 100 ppm, or less than 50 ppm, or less than 20 ppm.

In one embodiment, the polymer is a homopolymer of the first monomer. In another embodiment, the polymer is a copolymer such as a block copolymer or an alternating copolymer, where in the copolymer comprises at least one second monomer in addition to the first monomer.

In one embodiment, the conjugated polymer is an optionally substituted polythiophene, polypyrrole, or polydithieno[3,2-b:2',3'-d]pyrrole. In another embodiment, the conjugated polymer is a substituted polythiophene.

In a further embodiment, the conjugated polymer is regioregular. For example, the degree of regioregularity can be at least 60%, or at least 70%, or at least 80%, or at least 90%, or at least 95%, or at least 98%. In one embodiment, the conjugated polymer is regioirregular. The degree of regioregularity can be left than 50%, or less than 40%, or less than 30%.

The conjugated polymer can comprise, for example, at least 50, or at least 60, or at least 70, or at least 80, or at least 90, or at least 95, or at least 99 molar percent of repeat units based on the first monomer.

Examples of the conjugated polymer include the following:

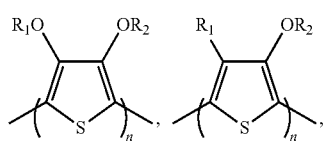

-continued

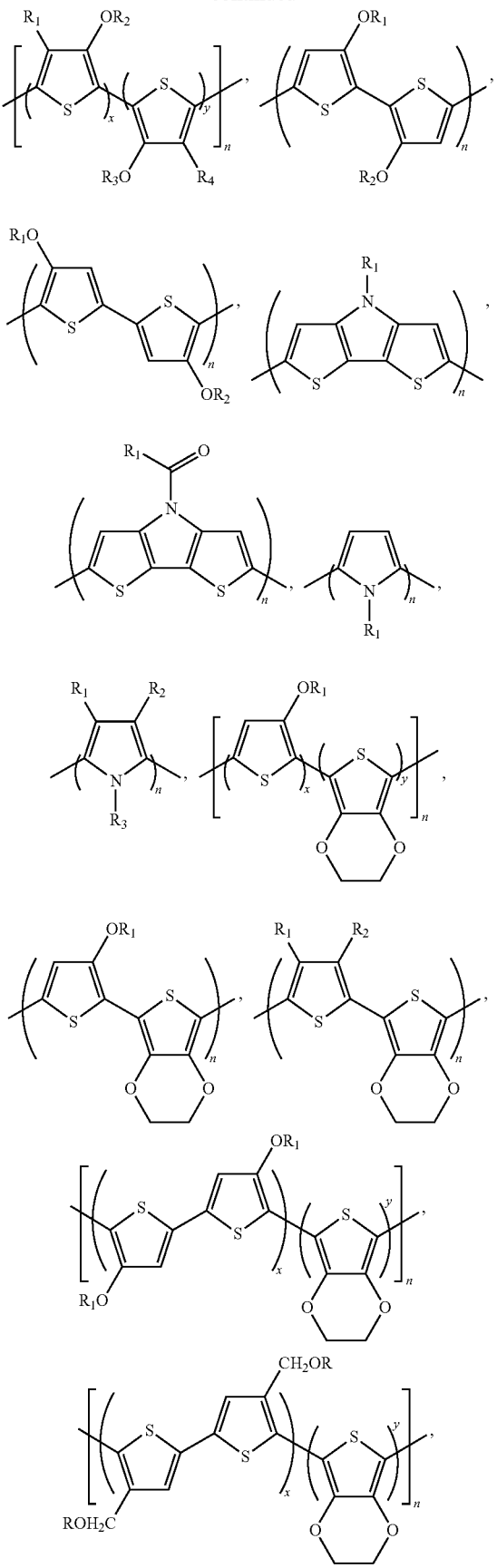

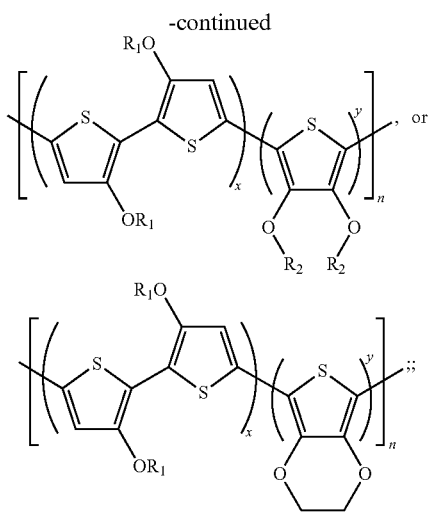

wherein n, x and y are each an integer of one or more; and wherein $R_1$, $R_2$, $R_3$ and $R_4$ are each independently a hydrogen or an optionally substituted linear, branched or cyclic alkyl, alkoxy, alkylthio, aryl, aryloxy, arylthio, acyl, ether, or polyether group.

In one embodiment, the conjugated polymer is not obtained by electrochemical polymerization, by transition-metal-promoted cross coupling of organic dihalide groups, or by oxidative chemical polymerization using metal-based oxidant.

In some embodiments, the conjugated polymer is a copolymer comprising a first thiophene repeat unit and a second thiophene repeat unit. The thiophene copolymer can be, for example, a block copolymer, an alternating copolymer, or a random copolymer. The first thiophene repeat unit can be, for example, 3,4-disubstituted thiophene. The second thiophene repeat unit can be, for example, 3-substituted thiophene. The thiophene copolymer can comprise, for example, a block of poly(3,4-disubstituted thiophene). The thiophene copolymer can comprise, for example, a block of regioregular poly(3-substituted thiophene). The thiophene copolymer can comprise, for example, a block of regioirregular poly(3-substituted thiophene).

In some embodiments, the conjugated polymer is made from a thiophene dimer. The two thiophene units in said dimer can be same or different.

In some embodiments, the conjugated polymer comprises thiophene repeat units that are sulfonated. The degree of sulfonation can be, for example 10-100%, or 30-95%, or 50-90%, or more than 75%. The sulfonated polymer can be made by, for example, replacing a hydrogen atom at the 4-position of a 3-substituted thiophene repeat unit with a sulfur acid functional group. The sulfonated polymer can be, for example, neutralized to a substantial neutral pH. The sulfonated polymer can be, for example, self-doped. The sulfonation of polythiophene is described in U.S. Pat. No. 8,017,241, which is hereby incorporated by reference in its entirety.

In some embodiments, the conjugated polymer comprises: (i) at least one first repeat unit represented by:

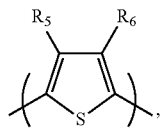

wherein $R_5$ and $R_6$ are each independently an optionally substituted linear, branched, or cyclic alkoxy, alkylene oxide or polyether; and (ii) at least one second repeat unit represented by

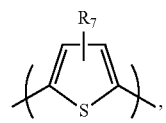

wherein $R_7$ is an optionally substituted linear, branched, or cyclic alkyl, alkoxy, alkylene oxide or polyether. The copolymer can be further doped including sulfonated. In one embodiment, the first repeating unit is 3,4-dipolyether-thiophene or 3,4-ethylenedioxy-thiophene. In one embodiment, the second repeat unit is 3-alkyl-thiophene, 3-polyether-thiophene, or a 3-substituted thiophene comprising at least one fluorinated group (e.g., 3-(2,2,2-trifluoroethoxy) thiophene).

Devices, Methods of Use, Applications

Embodiments described herein can be applied to, for example, conjugated conductive polymers with reduced band gaps, low oxidation potentials, and/or a highly stable conducting state, such as alkoxy- or polyether-substituted polythiophenes, polypyrroles, poly(dithieno[3,2-b:2',3'-d]pyrrole), polyisothionaphthalene, etc., which can be used in HILs (hole injection layers), HTLs (hole transport layers), transparent conductive oxides (TCO, since these polymers become nearly transparent in the oxidized form), Li-batteries, capacitors, and other organic electronics applications. Devices can be prepared including, for example, OLED (organic light emitting device) devices, organic photovoltaic devices, and transistors.

In some embodiments, the conjugated polymers, including polythiophenes, described herein can be used in batteries, including primary and secondary batteries, and also including, for example, lithium-ion batteries. They can be used in the anode or cathode. The cathode of the battery can comprise, for example, a composition comprising one or more of the polythiophene described herein. The cathode composition can further comprise, for example, a binder (e.g., PVDF) and an active material (e.g., LiCoO2) mixed with the conjugated polymer (e.g., polythiophene). Fluorinated or non-fluorinated polymers can be used. In one embodiment, a polythiophene can comprise, for example, at least one fluorinated group. In some embodiments, the polythiophene can be, for example, a copolymer or homopolymer comprising at least one 3-substituted thiophene repeating unit, wherein the 3-substituent comprises a fluorinated alkoxy or polyether group. 3,4-Substituted polymers also can be used. In some embodiments, such as the anode for example, the polythiophene can comprise, for example, at least one sulfonate group directly bonded to the thiophene ring. Crown ether substituents can be used, wherein the crown ether can be, for example, adapted for binding to lithium.

In some embodiments, the conjugated polymers (e.g., polythiophenes) described herein can be used in capacitors. The cathode of the capacitor can comprise, for example, a composition comprising the polythiophene described herein. The polythiophene can comprise, for example, at least one 3,4-ethylenedioxythiophene repeating unit. The polythiophene can be, for example, an oligomer comprising at least three or at least four 3,4-ethylenedioxythiophene repeating unit. In some embodiments, a polythiophene can comprise, for example, at least one sulfonate group directly bonded to the thiophene ring.

In some embodiments, the polythiophene described herein is used in OLED devices. The OLED devices can comprise, for example, a cathode, an anode, an emissive layer, and a hole injection layer, wherein the hole injection layer comprises the polythiophene described herein. The polythiophene can be, for example, a copolymer or homopolymer comprising at least one 3-substituted thiophene, wherein the 3-substituent comprises an alkyl, alkoxy, polyether or alkylene oxide. The polythiophene can be, for example, a copolymer or homopolymer comprising at least one 3,4-disubstituted thiophene, wherein the substituents are selected from alkoxy, polyether and alkylene oxide. The polythiophene can comprise, for example, at least one sulfonation group directly bonded to the thiophene ring.

In general, the widely-used synthetic methodologies for producing these materials are based on transition metal promoted cross-coupling of organic dihalide derivatives of functionalized polymer precursors. Even though these techniques allow synthesis of processable and regio-specific materials, they can be limited to monomeric precursors with low oxidation potentials, especially in their halogenated state. Also, due to limited stability, synthesis and purification of halogenated monomers can become cumbersome and very expensive and thereby limits its usefulness in many commercial applications.

Additional embodiments are provided in the following working examples.

WORKING EXAMPLES

Example 1

Synthesis of poly{3-[2-(2-methoxyethoxy)ethoxy]thiophene} [PMEET]

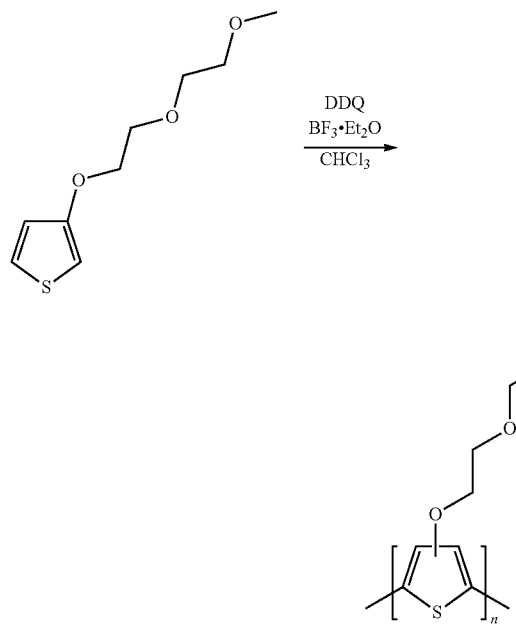

A dry 100-mL three-neck flask equipped with an addition funnel was flushed with $N_2$ and was charged with 3-[2-(2-methoxyethoxy)ethoxy]thiophene (0.20 g, 1.0 mmol), boron trifluoride etherate $(BF_3.O(Et)_2)$ (0.5 mL, 4.0 mmol) and anhydrous $CHCl_3$ (20 mL, 0.05 M) via deoxygenated syringe. The reaction flask was cooled to 0° C. and a 0.05 M suspension of 2,3-dichloro-5,6-dicyanobenzoquinone (DDQ) in $CHCl_3$ (80 mL, 4.0 mmol) was added drop-wise via deoxygenated syringe. Formation of black precipitate was noticed within 1 hour upon addition of DDQ. After addition was completed, stirring was continued for 24 hours, at which point the reaction mixture was poured into 200 mL of hexanes forming fine black particles. The combined organic solid was washed with hexanes two times and dried. The crude product was re-dissolved in minimal amount of methanol and precipitated in water. The polymer was collected via filtration and washed thoroughly with hot water. The residue was dedoped by stirring in 100 mL of water with 2 mL of hydrazine monohydrate for 1 hour. The dark solid was isolated by filtration and washed with water again. After being dried under vacuum, the polymer was analyzed by GPC in NMP with 1 mmol/L LiBr ([c]=0.8 mg/mL, rate 1 mL/min, at 80° C.) vs. polystyrene standards: $M_n$=17,900, $M_w$=35,850, PDI=1.9.

Spectral data: $^1H$ NMR (300 MHz, $CDCl_3$): $\delta_H$ 3.39 (s, 3H), 3.59 (bm, 2H), 3.79 (bm, 2H), 3.96 (bm, 2H), 4.34 (bm, 2H), 6.98 (bm, 1H).

Figure 1B:
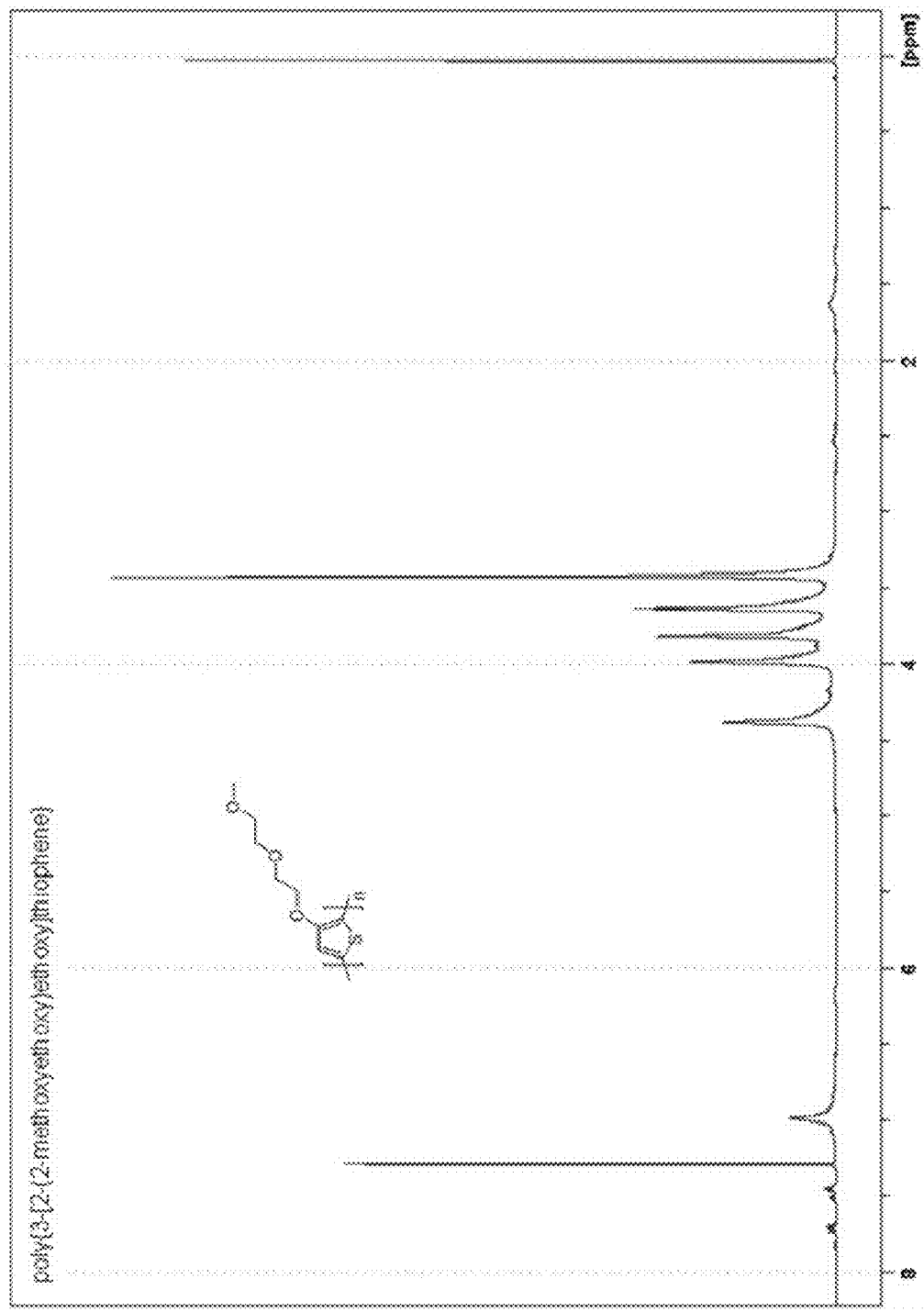
FIG. 1b shows $^1$H NMR (500 MHz) spectra of poly{3-[2-(2-methoxyethoxy)ethoxy]thiophene} (PMEET) synthesized via GRIM method.

NMR spectral data confirmed the structural integrity and regio-irregular microstructure of the polymer (FIG. 1a) and then compared to a regioregular polymer prepared by GRIM method (FIG. 1b).

Example 2

Solvent free synthesis of poly{3-[2-(2-methoxyethoxy)ethoxy]thiophene} [PMEET]

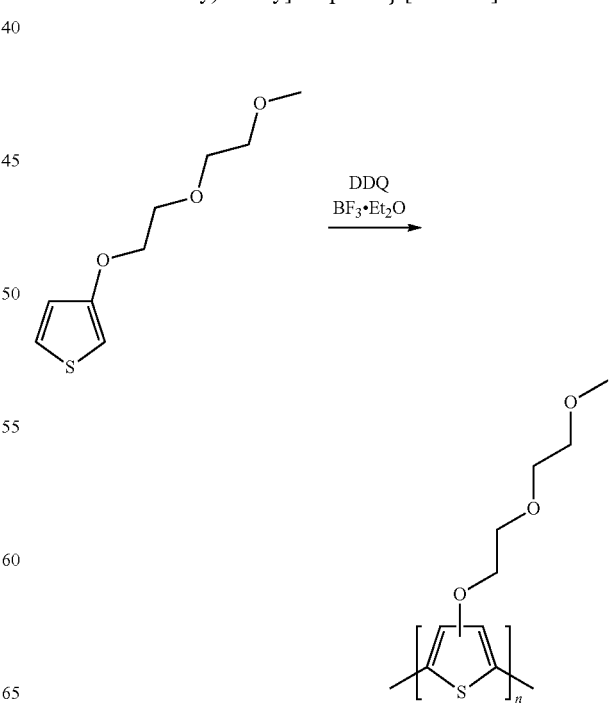

A dry 250-mL three-neck flask equipped with a mechanical stirrer and a thermo-couple was flushed with $N_2$ and charged with 3-[2-(2-methoxyethoxy)ethoxy]thiophene (20 g, 0.099 mol) and boron trifluoride etherate ($BF_3 \cdot O(Et)_2$) (50 mL, 0.41 mol). 2,3-Dichloro-5,6-dicyanobenzoquinone (DDQ) (27.86 g, 0.123 mol) was added in five portions. The reaction was exothermic and DDQ was added such that the reaction temperature was either stabilized and/or started to decrease before each consecutive addition. Formation of black precipitate was observed as the first portion of DDQ was added. After addition was completed, temperature was set at 60° C. and stirring was continued for 24 hours, at which point most of material solidified. The reaction mixture was quenched by addition Zinc powder (16.1 g, 0.246), and the reaction mixture was stirred for an additional hour. The mixture was filtered and organic solid was extensively washed in sequence with methanol, 10% HCl (aq), hot water. A Soxhlet extraction was then performed overnight on the polymer to remove residual DDQ. The solids were then collected from the thimble and rinsed with water and IPA. The polymer was then reduced by stirring in 100 mL of water with 2 mL of hydrazine monohydrate for 1 hour. The dark solid was isolated by filtration and washed with water again until pH was neutral. After being dried under vacuum, 10.1 g (51% yield) of polymer was isolated and analyzed by GPC in NMP with 1 mmoL/L LiBr (0.8 mL/min at 80° C.) vs. polystyrene standards: $M_n$=18,015, $M_w$=24,435, PDI=1.36.

Spectral data: $^1$H NMR (500 MHz, $CDCl_3$): $\delta_H$ 3.39 (bs, 3H), 3.59 (bm, 2H), 3.79 (bm, 2H), 3.96 (bm, 2H), 4.34 (bm, 2H), 6.9-7.1 (bm, 1H).

Example 3

Synthesis of poly{3,4-bis[2-(2-butoxyethoxy)ethoxy]thiophene} [PdiBEET]

A dry 100-mL three-neck flask was flushed with $N_2$ and was charged with 3,4-bis[2-(2-butoxyethoxy)ethoxy]thiophene (1.83 g, 4.50 mmol), boron trifluoride etherate ($BF_3 \cdot O(Et)_2$) (1.40 mL, 11.1 mmol) and anhydrous $CHCl_3$ (20 mL, 0.23 M) via deoxygenated syringe. 2,3-Dichloro-5,6-dicyanobenzoquinone (DDQ) (3.1 g, 13.6 mmol) was added in small portions. Polymerization was carried out at room temperature (about 25° C.). Formation of black precipitate was noticed within 1 hour upon addition of DDQ. After addition was completed, stirring was continued for 24 hours, and the reaction mixture was poured into 200 mL of water:methanol (50:50) mixture to quench and precipitate the polymer. The organic solid was isolated and was washed thoroughly with hot water. The residue was dedoped by stirring in 200 mL of water with 2 mL of hydrazine monohydrate for 1 hour. The polymer was re-dissolved in minimal amount of $CHCl_3$ and precipitated in methanol:water (50:50) mixture. The dark solid was isolated by filtration and washed with water again. After being dried, the polymer was Soxhlet extracted with hexanes, dried under vacuum, and analyzed by GPC in chlorobenzene (1 mL/min at 80° C.) vs. polystyrene standards: $M_n$=14,400, $M_w$=22,900, PDI=1.6.

Spectral data: $^1$H NMR (300 MHz, $CDCl_3$): $\delta_H$ 0.89 (t, 6H), 1.34 (t, 4H), 1.54 (bt, 4H), 3.43 (bm, 4H), 3.56 (bm, 4H), 3.68 (bm, 4H), 3.89 (bm, 4H), 4.38 (bm, 4H).

Figure 2A:
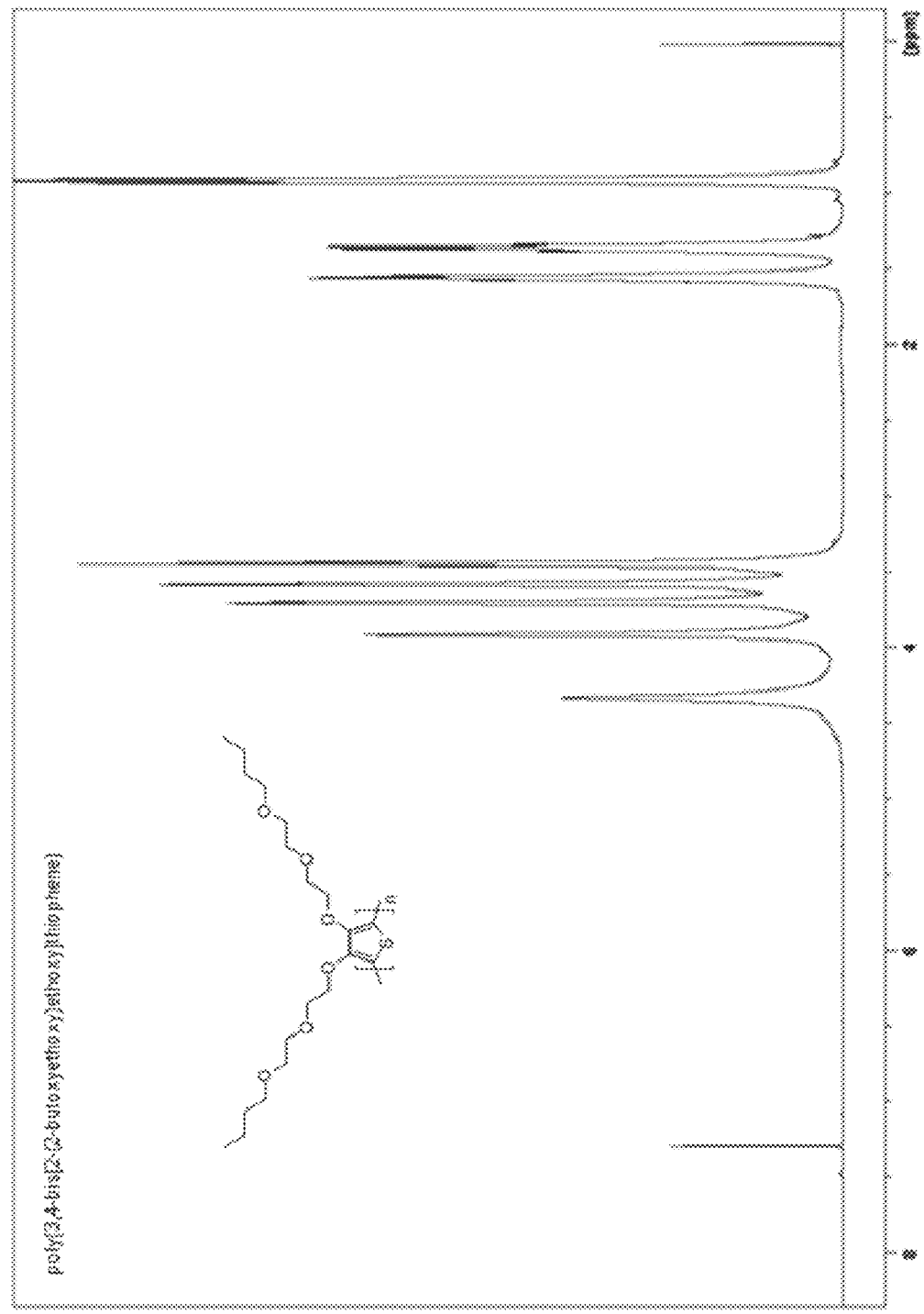
FIG. 2a shows $^1$H NMR (500 MHz) spectra of poly{3,4-bis[2-(2-butoxyethoxy)ethoxy]thiophene} (PdiBEET) synthesized via oxidative method.
Figure 2B:
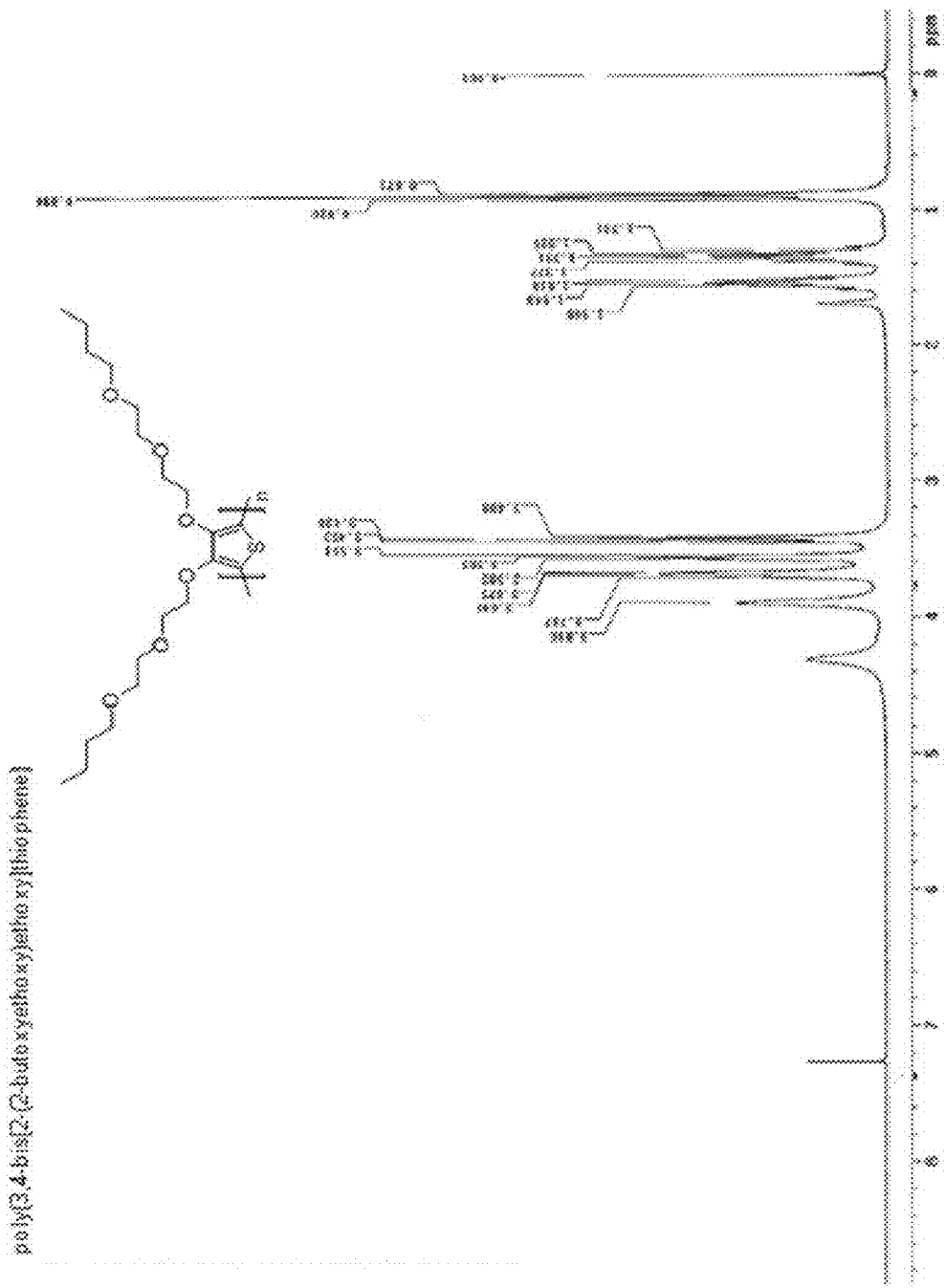
FIG. 2b shows $^1$H NMR (500 MHz) spectra of poly{3,4-bis[2-(2-butoxyethoxy)ethoxy]thiophene} (PdiBEET) synthesized via GRIM method.

NMR spectral data confirmed the structural integrity of the polymer (FIG. 2a) compared to polymer prepared by GRIM method (FIG. 2b).

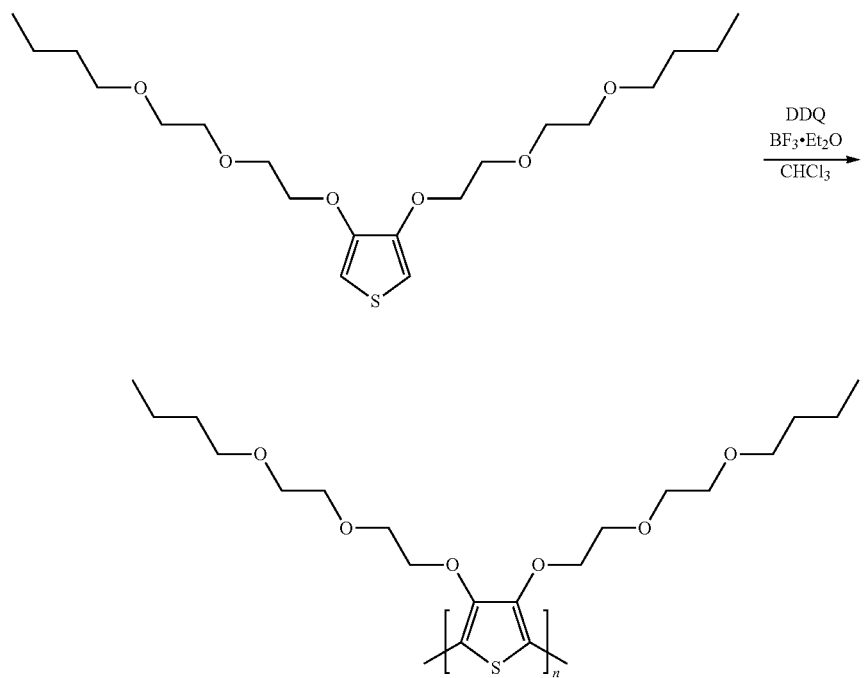

Example 4

Synthesis of poly{3,4-bis[2-(2-butoxyethoxy)ethoxy]thiophene} [PdiBEET]

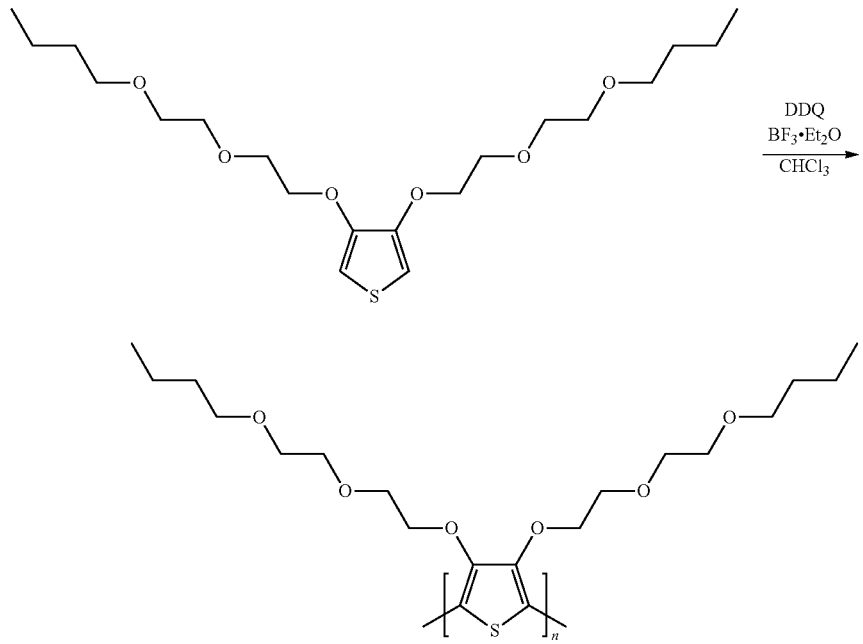

A dry 250-mL three-neck flask equipped with addition funnel, nitrogen adapter, and a stirring bar, was flushed with $N_2$ and was charged with 3,4-bis[2-(2-butoxyethoxy)ethoxy]thiophene (2.00 g, 4.90 mmol), boron trifluoride etherate ($BF_3 \cdot O(Et)_2$) (2.48 mL, 19.8 mmol) and anhydrous $CHCl_3$ (100 mL, 0.05 M) via deoxygenated syringe. 2,3-Dichloro-5,6-dicyanobenzoquinone (DDQ) (4.49 g, 19.8 mmol) was dispersed in 100 mL of $CHCl_3$ (0.2 M) in a separate 250 mL 3-neck round bottom flask under inert atmosphere. Dispersion of DDQ in chloroform was transferred into the addition funnel via deoxygenated cannula. Subsequently, DDQ was added drop-wise to the reaction flask. Formation of black precipitate was noticed within 1 hour upon addition of DDQ. After addition was completed, stirring was continued for 48 hours, at which point ferrocene (19.8 mmol) was added to the reaction and it was poured into 500 mL of water:methanol (50:50) mixture, excess of chloroform was removed under reduced pressure to precipitate the polymer. The organic solid was isolated and was washed thoroughly with hot water. The residue was dedoped by stirring in 200 mL of water with 2 mL of hydrazine monohydrate for 1 hour (this procedure was repeated at least two more times). The polymer was re-dissolved in minimal amount of $CHCl_3$ and precipitated in methanol:water (50:50) mixture (the procedure can be repeated to assure removal of residual ferrocene). The dark solid was isolated by filtration and washed with water again and dried under vacuum to yield 1.42 g (72%) of polymer. The polymer was analyzed by GPC in NMP with 1 mmol/L LiBr ([c]=0.8 mg/mL, rate 1 mL/min at 80° C.) vs. polystyrene standards: $M_n$=33,800, $M_w$=52,600, PDI=1.6.

Spectral data: $^1$H NMR (300 MHz, $CDCl_3$): $\delta_H$ 0.89 (t, 6H), 1.34 (t, 4H), 1.54 (bt, 4H), 3.43 (bm, 4H), 3.56 (bm, 4H), 3.68 (bm, 4H), 3.89 (bm, 4H), 4.38 (bm, 4H).

Example 5

Synthesis of poly{3,4-bis[2-(2-butoxyethoxy)ethoxy]thiophene} [PdiBEET]

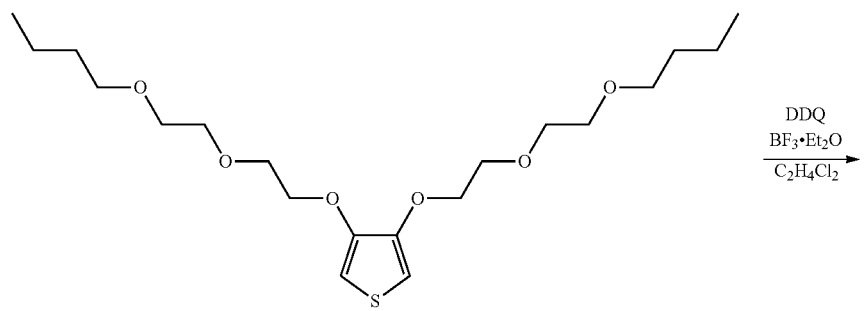

-continued

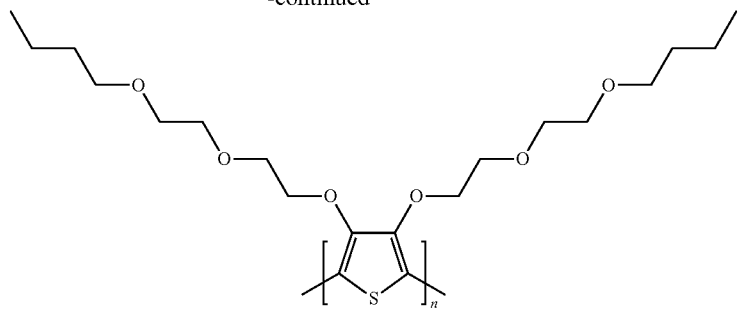

A dry 250-mL three-neck flask equipped with a magnetic stirrer, thermocouple, septum, and reflux condenser. The flask was flushed with $N_2$ and was charged with 3,4-bis[2-(2-butoxyethoxy)ethoxy]thiophene (10.00 g, 0.0247 mol), boron trifluoride etherate ($BF_3 \cdot O(C_2H_5)_2$) (12.19 mL, 0.0988 mol) and anhydrous $C_2H_4Cl_2$ (70 mL, 0.3 M) via deoxygenated syringe. Next, 2,3-dichloro-5,6-dicyanobenzoquinone (DDQ) (6.96 g, 0.031 mol) was split into 5 equal portions. One portion was added to the reaction mixture every five minutes for 20 minutes. Mixture began to darken upon addition of DDQ, and an increase in viscosity was observed ~15 min after the last addition. After DDQ addition was completed, the mixture was stirred for 3 hours at room temperature. After three hours, ferrocene (11.52 g, 0.062 mol) was added all at once. The mixture was stirred for an additional hour at room temperature. Next, the reaction mixture was added to a 500 mL beaker containing 200 mL DI water, and the mixture was stirred for 5 minutes. The mixture was then concentrated by rotary evaporation until all the ethylene chloride had dissolved and the round bottom flask contained a suspension of black solids in water. The mixture was then filtered and the recovered solids were dissolved in a minimal amount of chloroform. The mixture was passed through a 350 mL silica plug (coarse silica gel) with chloroform. DI water (300 mL) was added to the collected eluent and the mixture was concentrated by rotary evaporation (water is added to keep solids from adhering to the sides of the round bottom flask during solvent evaporation). After all the chloroform had evaporated and the flask contained only water and black solid material, the mixture was filtered. The recovered solids were dissolved in a minimal amount of chloroform. This mixture was again passed through silica gel using the aforementioned procedure. The recovered solids were then washed with 50 mL IPA in 400 mL 1% HCl (aq) at 50° C. for 2 hours. The mixture was filtered and recovered solids were added to 50 mL IPA in 300 mL 5% hydrazine (aq) and stirred at 40° C. for 1 hour. The mixture was filtered and recovered solids were washed in 50 mL IPA in 300 mL DI water for 1 hour at 40° C. for 1 hour. The mixture was filtered and recovered solids were dried overnight in a vacuum oven at 60° C. The polymer was analyzed by GPC in NMP with 1 mmol/L LiBr ([c]=0.8 mg/mL, rate 0.8 mL/min at 80° C.) vs. polystyrene standards: $M_n$=38,839, $M_w$=72,210, PDI=1.9.

Spectral data: $^1$H NMR (500 MHz, $CDCl_3$): $\delta_H$ 0.895 (t, 6H), 1.35 (m, 4H), 1.54 (m, 4H), 3.43 (t, 4H), 3.58 (m, 4H), 3.69 (m, 4H), 3.83 (m, 4H), 4.31 (m, 4H).

Example 6

Synthesis of poly{3,4-bis[2-(2-butoxyethoxy)ethoxy]thiophene} [PdiBEET]

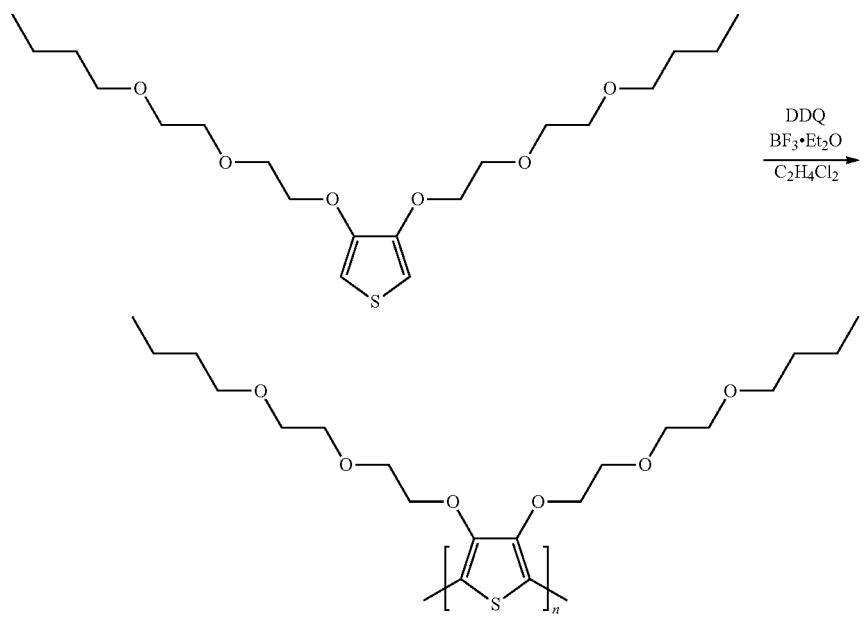

A dry 250-mL three-neck flask equipped with a magnetic stirrer, thermocouple, septum, and reflux condenser. The flask was flushed with $N_2$ and was charged with 3,4-bis[2-(2-butoxyethoxy)ethoxy]thiophene (10.00 g, 0.0247 mol), boron trifluoride etherate ($BF_3 \cdot O(Et)_2$) (12.19 mL, 0.0988 mol) and anhydrous $C_2H_4Cl_2$ (70 mL, 0.3 M) via deoxygenated syringe. Next, 2,3-dichloro-5,6-dicyanobenzoquinone (DDQ) (6.96 g, 0.031 mol) was split into 5 equal portions. One portion was added to the reaction mixture every five minutes for 20 minutes. Mixture began to darken upon addition of DDQ, and an increase in viscosity was observed ~15 min after the last addition. After DDQ addition was completed, the mixture was stirred for 3 hours at room temperature. After three hours, Zn (powder, 4.05 g, 0.062 mol) was added all at once. The mixture was stirred for an additional hour at room temperature. Next, the reaction mixture was added to a 500 mL beaker containing 200 mL DI water, and the mixture was stirred for 5 minutes. The mixture was then concentrated by rotary evaporation until all the ethylene chloride had dissolved and the round bottom flask contained a suspension of black solids in water. The mixture was then filtered and the recovered solids were dissolved in a minimal amount of chloroform. The mixture was passed through a 350 mL silica plug (coarse silica gel) with chloroform. DI water (300 mL) was added to the collected eluent and the mixture was concentrated by rotary evaporation (water is added to keep solids from adhering to the sides of the round bottom flask during solvent evaporation). After all the chloroform had evaporated and the flask contained only water and black solid material, the mixture was filtered. The recovered solids were dissolved in a minimal amount of chloroform. This mixture was again passed through silica gel using the aforementioned procedure. The recovered solids were then washed twice with 50 mL IPA in 400 mL 1% HCl (aq) at 50° C. for 2 hours. The mixture was filtered and recovered solids were added to 50 mL IPA in 300 mL 5% hydrazine (aq) and stirred at 40° C. for 1 hour. The mixture was filtered and recovered solids were washed in 50 mL IPA in 300 mL DI water for 1 hour at 40° C. for 1 hour. The mixture was filtered and recovered solids were dried overnight in a vacuum oven at 60° C. The polymer was analyzed by GPC in NMP with 1 mmol/L LiBr ([c]=0.8 mg/mL, rate 0.8 mL/min at 80° C.) vs. polystyrene standards: $M_n$=25,689, $M_w$=47,821, PDI=1.86.

Spectral data: $^1$H NMR (500 MHz, $CDCl_3$): $\delta_H$ 0.89 (t, 6H), 1.35 (m, 2H), 1.54 (m, 4H), 3.43 (t, 4H), 3.58 (m, 4H), 3.69 (m, 4H), 3.83 (m, 4H), 4.31 (m, 4H).

Example 7

Synthesis of poly{3,4-bis[2-(2-butoxyethoxy)ethoxy]thiophene-r-3-[2-(2-butoxyethoxy)ethoxy]thiophene} [P(diBEET-r-BEET)]

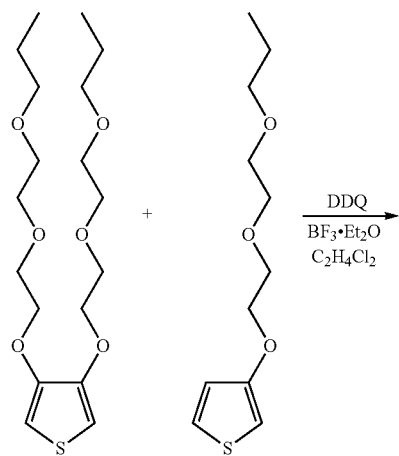

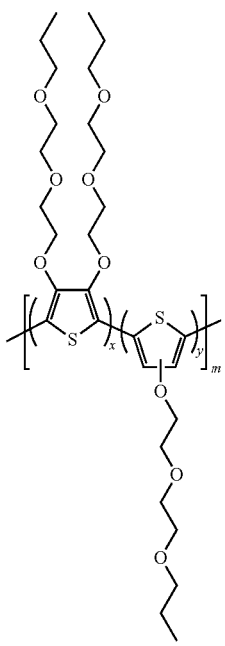

A dry 250-mL three-neck flask equipped with a magnetic stirrer, thermocouple, septum, and reflux condenser. The flask was flushed with $N_2$ and was charged with 3,4-bis[2-(2-butoxyethoxy)ethoxy]thiophene (10.00 g, 0.0247 mol), 3-[2-(2-butoxyethoxy)ethoxy]thiophene (0.669 g, 0.00275 mol), boron trifluoride etherate ($BF_3 \cdot O(Et)_2$) (13.55 mL, 0.110 mol) and anhydrous $C_2H_4Cl_2$ (70 mL, 0.3 M) via deoxygenated syringe. Next, 2,3-dichloro-5,6-dicyanobenzoquinone (DDQ) (7.72 g, 0.034 mol) was split into 5 equal portions. One portion was added to the reaction mixture every five minutes for 20 minutes. Mixture began to darken upon addition of DDQ, and an increase in viscosity was observed ~15 min after the last addition. After DDQ addition was completed, the mixture was stirred for 3 hours at room temperature. After three hours, Zn (powder, 4.45 g, 0.068 mol) was added all at once. The mixture was stirred for an additional hour at room temperature. Next, the reaction mixture was added to a 500 mL beaker containing 200 mL DI water, and the mixture was stirred for 5 minutes. The mixture was then concentrated by rotary evaporation until all the ethylene chloride had dissolved and the round bottom flask contained a suspension of black solids in water. The mixture was then filtered and the recovered solids were dissolved in a minimal amount of chloroform. The mixture was passed through a 350 mL silica plug (coarse silica gel) with chloroform. DI water (300 mL) was added to the collected eluent and the mixture was concentrated by rotary evaporation (water is added to keep solids from adhering to the sides of the round bottom flask during solvent evaporation). After all the chloroform had evaporated and the flask contained only water and black solid material, the mixture was filtered. The recovered solids were dissolved in a minimal amount of chloroform and again passed through silica gel using the aforementioned procedure. The recovered solids were then washed twice with 50 mL IPA in 400 mL 1% HCl (aq) at 50° C. for 2 hours. The mixture was filtered and recovered solids were added to 50 mL IPA in 300 mL 5% hydrazine (aq) and stirred at 40° C. for 1 hour. The mixture was filtered and recovered solids were washed in 50 mL IPA in 300 mL DI water for 1 hour at 40° C. for 1 hour. The mixture was filtered and recovered solids were dried overnight in a vacuum oven at 60° C. The polymer was analyzed by GPC in NMP with 1 mmol/L LiBr ([c]=0.8 mg/mL, rate 0.8 mL/min at 80° C.) vs. polystyrene standards: $M_n$=33,490, $M_w$=61,117, PDI=1.86.

Figure 3A:
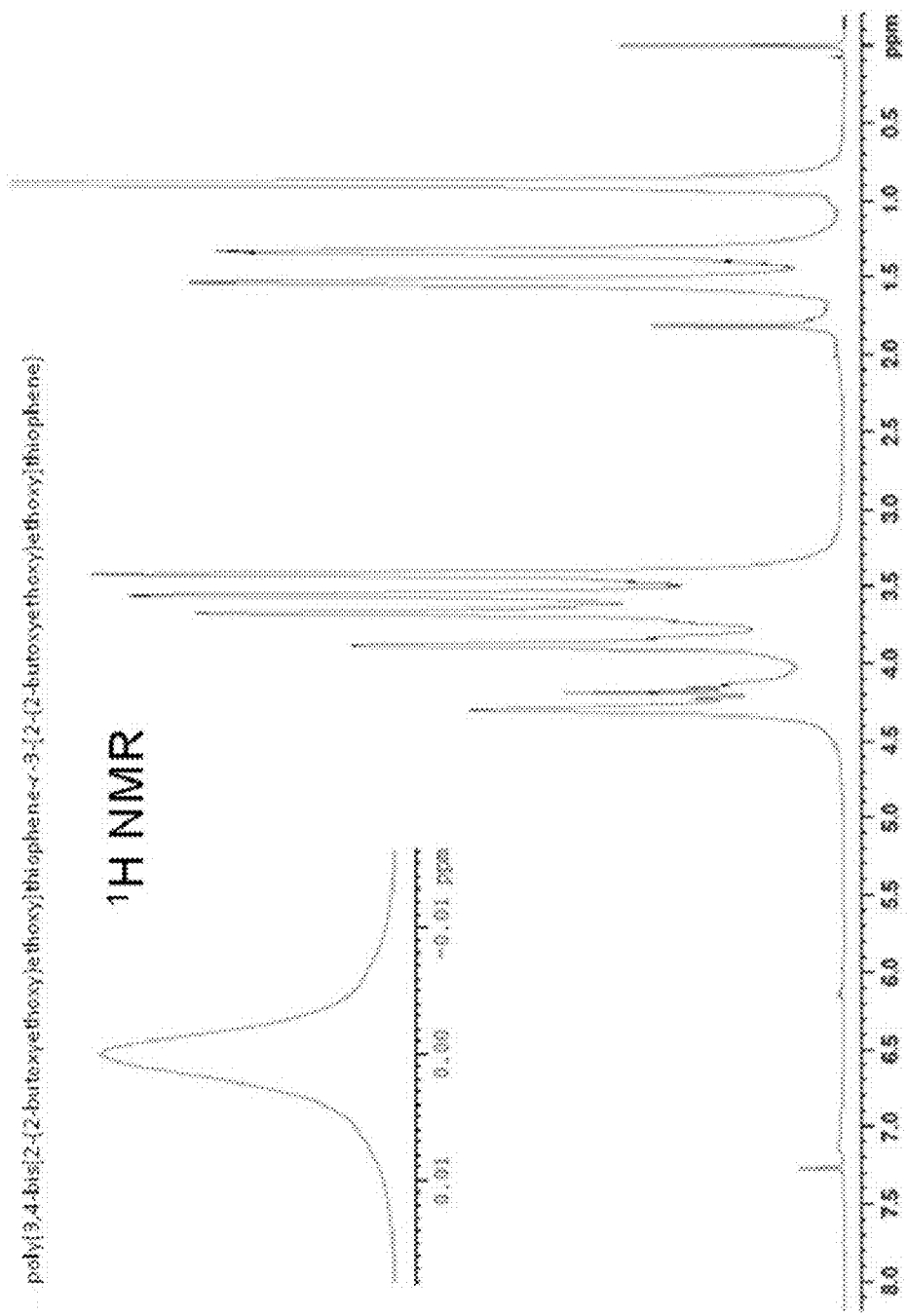
FIG. 3a shows $^1$H NMR (500 MHz) spectra of poly{3,4-bis[2-(2-butoxyethoxy)ethoxy]thiophene-co-3-[2-(2-butoxyethoxy)ethoxy]thiophene} synthesized via oxidative method.
Figure 3B:
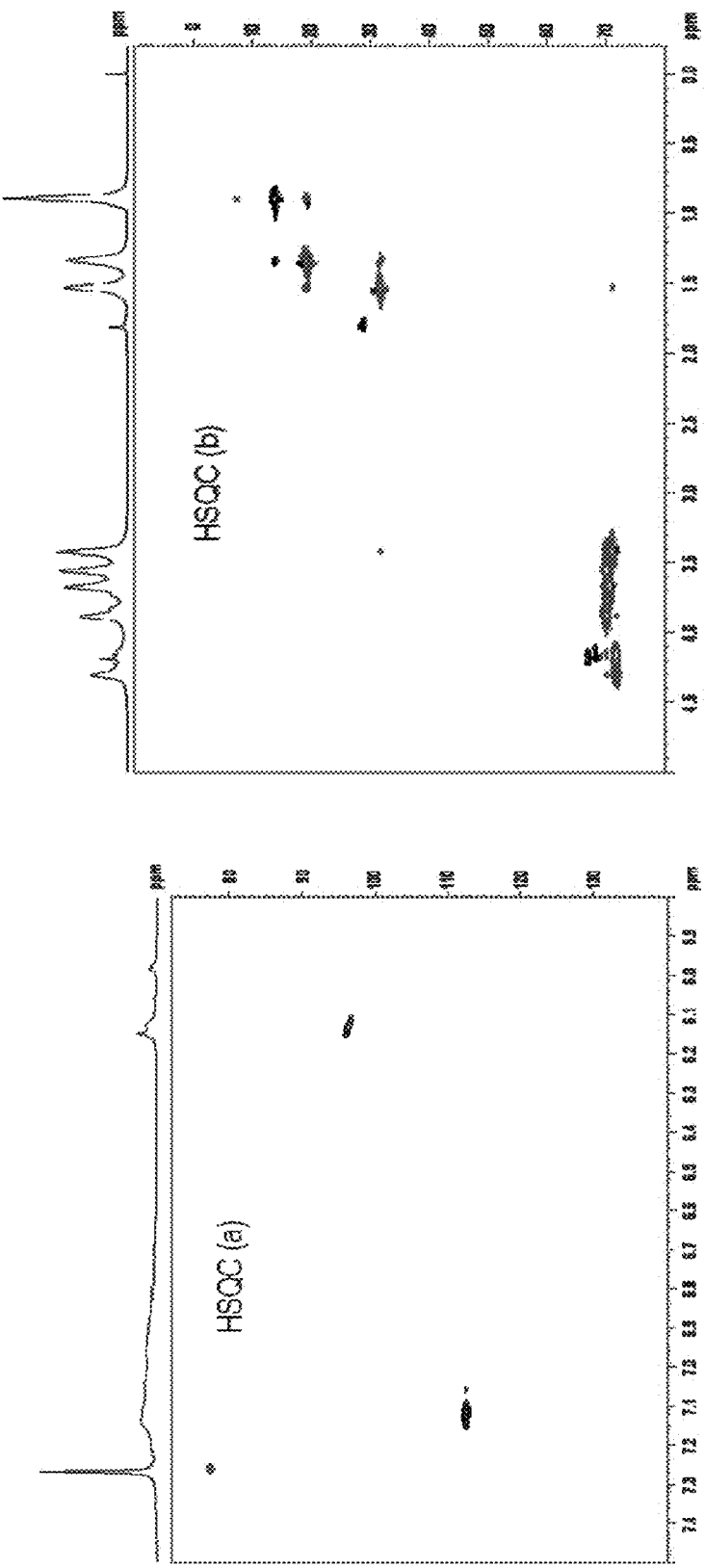
FIG. 3b shows $^1$H NMR (500 MHz) HSQC of poly{3,4-bis[2-(2-butoxyethoxy)ethoxy]thiophene-co-3-[2-(2-butoxyethoxy)ethoxy]thiophene} synthesized via oxidative method.

Spectral data: $^1$H NMR (500 MHz, CDCl$_3$): $\delta_H$ 0.89 (t, 6H), 1.35 (m, 2H), 1.54 (m, 4H), 3.43 (t, 4H), 3.58 (m, 4H), 3.69 (m, 4H), 3.83 (m, 4H), 4.31 (m, 4H), 7.10 (bs, 0.1H). 1D $^1$H NMR and 2D HSQC NMR spectral data confirmed the structural integrity of the polymer and incorporation of 3-[2-(2-butoxyethoxy)ethoxy]thiophene comonomer into polymer backbone (FIGS. 3a and 3b, respectively).

Example 8

Solvent free synthesis of poly 3-(2,2,2-trifluoroethoxy)thiophene [P2EF3]

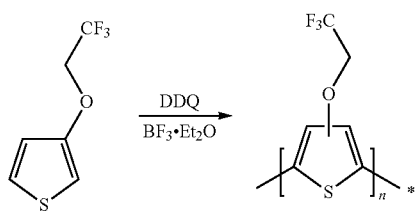

A dry 250-mL three-neck flask equipped with a mechanical stirrer, thermocouple, septum, N$_2$ inlet. The flask was flushed with N$_2$ and was charged with 3-(2,2,2-trifluoro) ethoxythiophene (10.00 g, 0.0549 mol) and boron trifluoride etherate (BF$_3$.O(Et)$_2$) (27.1 mL, 0.220 mol) via deoxygenated syringe. Next, 2,3-dichloro-5,6-dicyanobenzoquinone (DDQ) (15.45 g, 0.068 mol) was split into 5 equal portions. One portion was added to the reaction mixture every five minutes for 20 minutes. An increase in viscosity was observed ~15 min after the additions began. After DDQ addition was completed, the mixture was stirred for 3 hours at 60° C. After three hours, ferrocene (25.29 g, 0.136 mol) was added all at once. The mixture was stirred for an additional hour at room temperature. After one hour, 100 mL MeOH was added to the flask and the mixture was stirred an additional 15 minutes at room temperature. The contents of the flask were then transferred to a 1000 mL beaker using additional MeOH as necessary to wash the residual material into the beaker. More MeOH was added to the beaker until the total volume of the mixture was 500 mL. The mixture was then stirred 1 hour at 50° C. and then filtered. The recovered solids were combined with 400 mL MeOH, and the mixture was stirred at 50° C. for 1 hour. The mixture was filtered and the recovered solids were purified via soxhlet extraction with MeOH overnight. The solids remaining in the thimble were added to 200 mL MeOH and stirred at 50° C. for 1 hour. The mixture was filtered and the recovered solids were purified again by Soxhlet extraction overnight with MeOH. The solids remaining in the thimble were added to 200 mL MeOH and stirred at 50° C. for 1 hour. The mixture was filtered and the recovered solids were added to 300 mL 5% N$_2$H$_4$ (aq) and stirred at 50° C. for 1 hour. The mixture was filtered and the filtercake was rinsed twice with 100 mL DI water and once with 100 mL IPA. The recovered solids were dried overnight in a vacuum oven at 60° C. The polymer was analyzed by GPC in NMP with 1 mmol/L LiBr ([c]=0.8 mg/mL, rate 0.8 mL/min at 80° C.) vs. polystyrene standards: $M_n$=2,858, $M_w$=5,299, PDI=1.85.

Figure 4A:
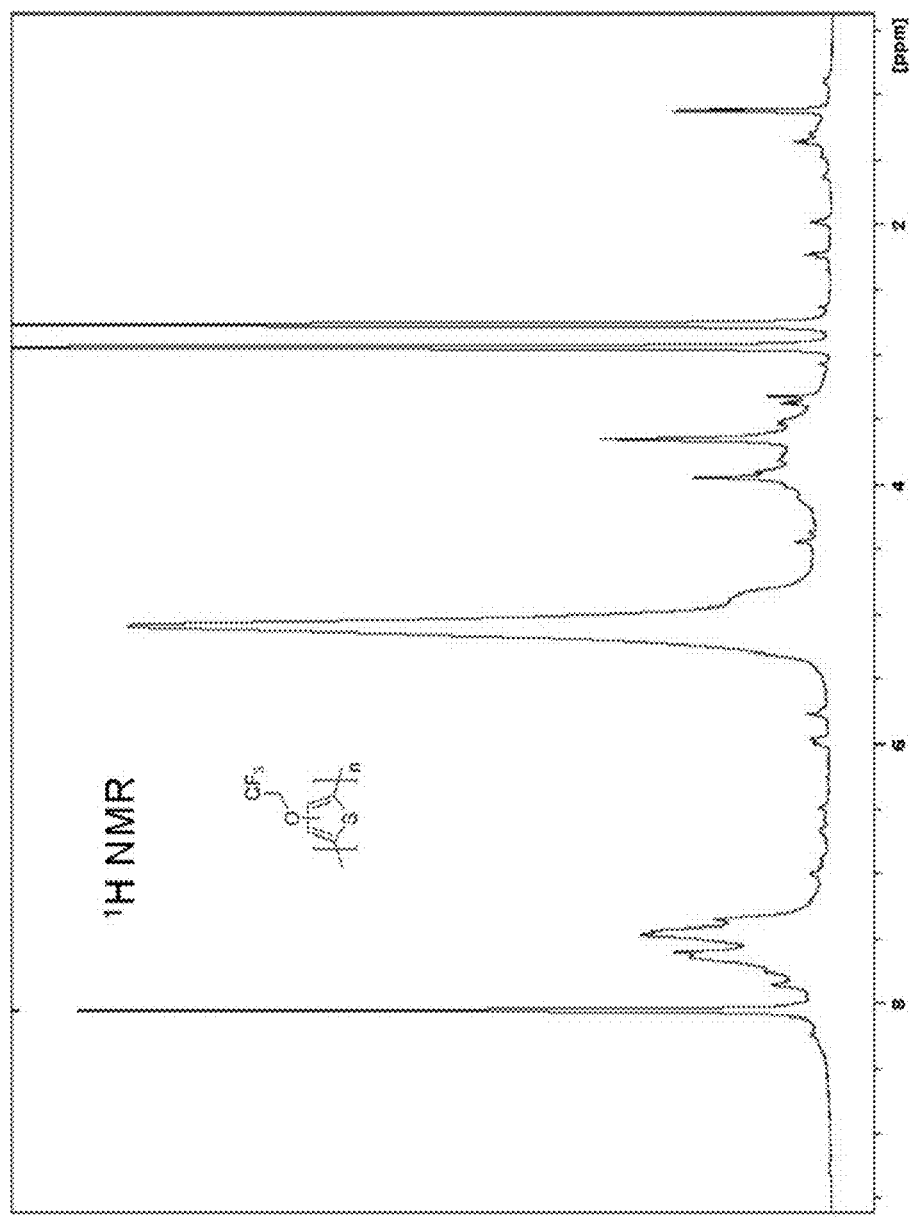
FIG. 4a shows $^1$H (500 MHz in DMF-d7) spectra of poly{3-(2,2,2-trifluoroethoxy)thiophene} (P2EF3) synthesized via oxidative method.
Figure 4B:
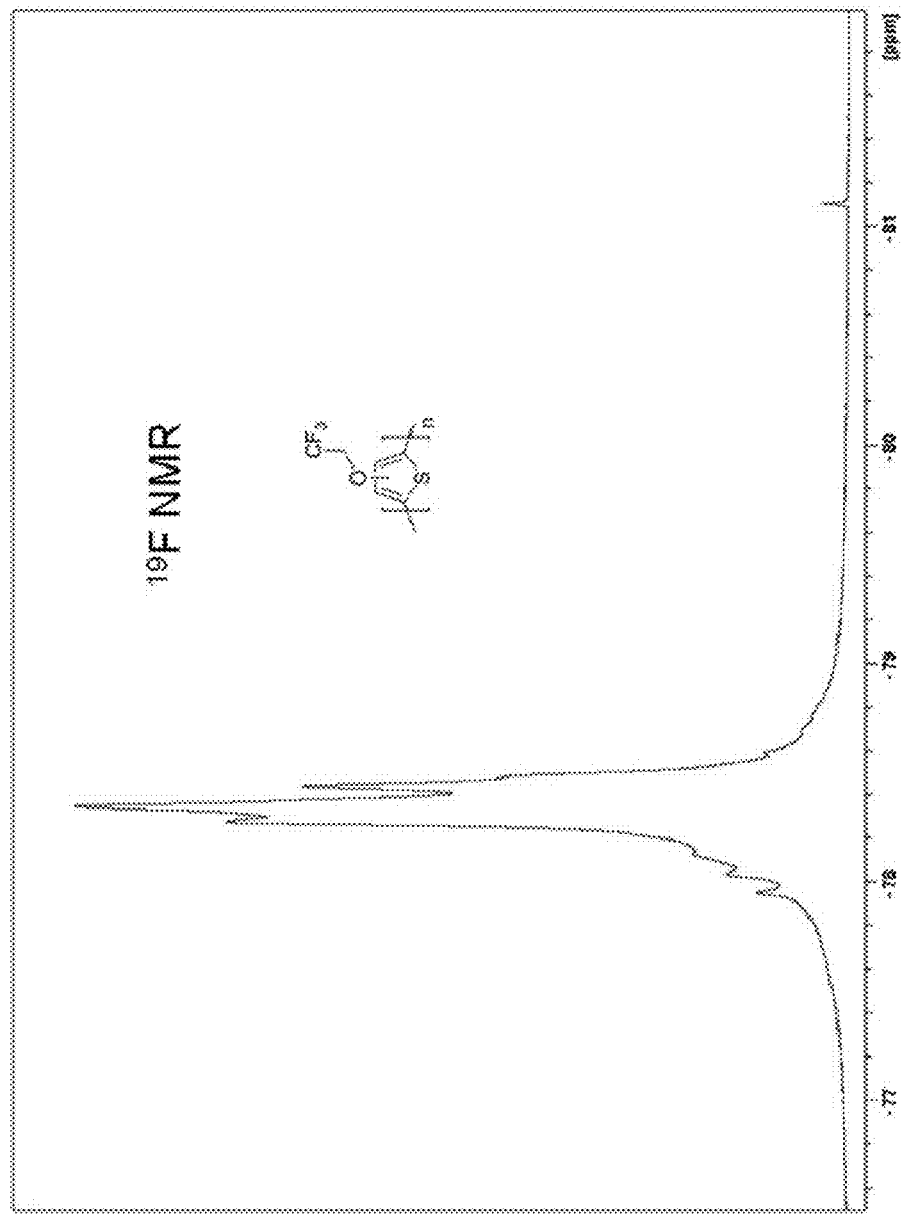
FIG. 4b shows $^{19}$F NMR (500 MHz in DMF-d7) spectra of poly{3-(2,2,2-trifluoroethoxy)thiophene} (P2EF3) synthesized via oxidative method.
Figure 4C:
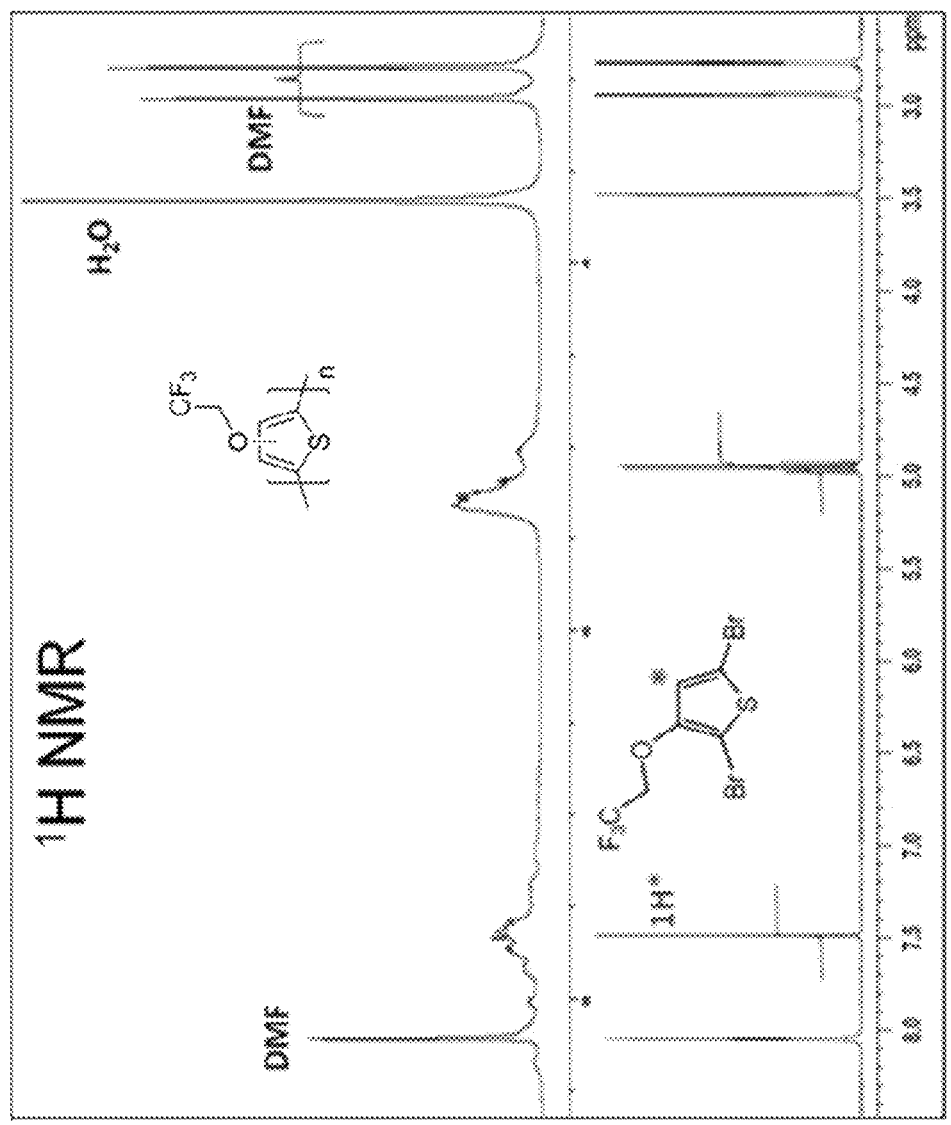
FIG. 4c shows $^1$H (500 MHz in DMF-d7) spectra of poly{3-(2,2,2-trifluoroethoxy)thiophene} (P2EF3) synthesized via GRIM method versus its monomer, 2,5-dibromo-3-(2,2,2-trifluoroethoxy)thiophene, indicating the differences in local magnetic environments between protons in the monomer and in the irregular polymer.
Figure 4D:
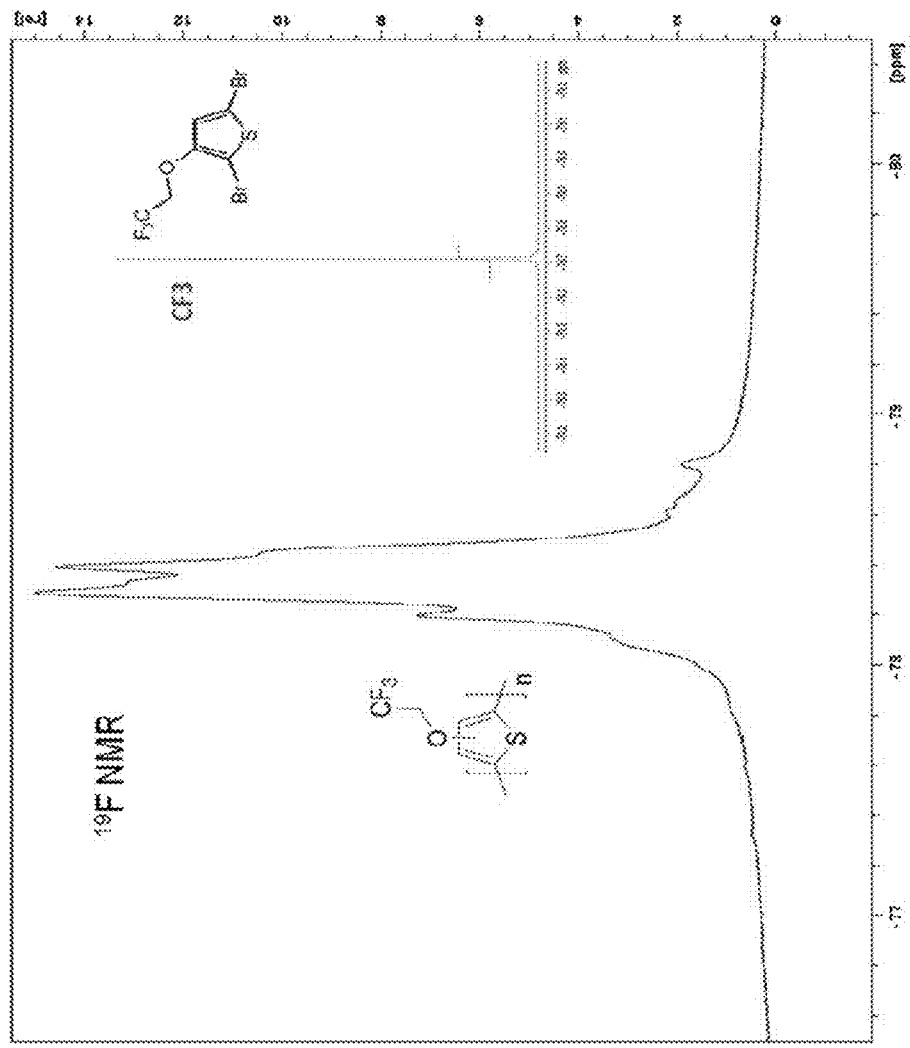
FIG. 4d shows $^{19}$F NMR (500 MHz in DMF-d7) spectra of poly{3-(2,2,2-trifluoroethoxy)thiophene} (P2EF3) synthesized via GRIM method versus its monomer, 2,5-dibromo-3-(2,2,2-trifluoroethoxy)thiophene, indicating the differences in local magnetic environments between protons in the monomer and in the irregular polymer.

Spectral data: $^1$H NMR (300 MHz, DMF-d7): $\delta_H$ 5.1 (bq, 2H), $\delta_H$ 7.5 (bm, 1H). $^1$H and $^{19}$F NMR spectral data confirmed the structural integrity and regio-irregular microstructure of the polymer (FIGS. 4a and 4b, respectively) and then compared to a comparatively regioirregular polymer prepared by GRIM method (FIGS. 4c and 4d) {where GRIM method (c-d) is pictured versus its monomer, 2,5-dibromo-3-(2,2,2-trifluoroethoxy)thiophene, indicating the differences in local magnetic environments between protons in the monomer and in the irregular polymer.

Example 9

Comparison of Polymers Prepared in Examples 1-8 with Polymers Prepared by GRIM Method As shown in Tables 1, 2, 3, and 4 polythiophene-based polymers produced by oxidative polymerization has similar material properties as those produced by traditional GRIM method. However, the impurity level of metal and/or halogen in polymers produced by oxidative polymerization is significantly less than GRIM-produced polymers.

Figure 5:
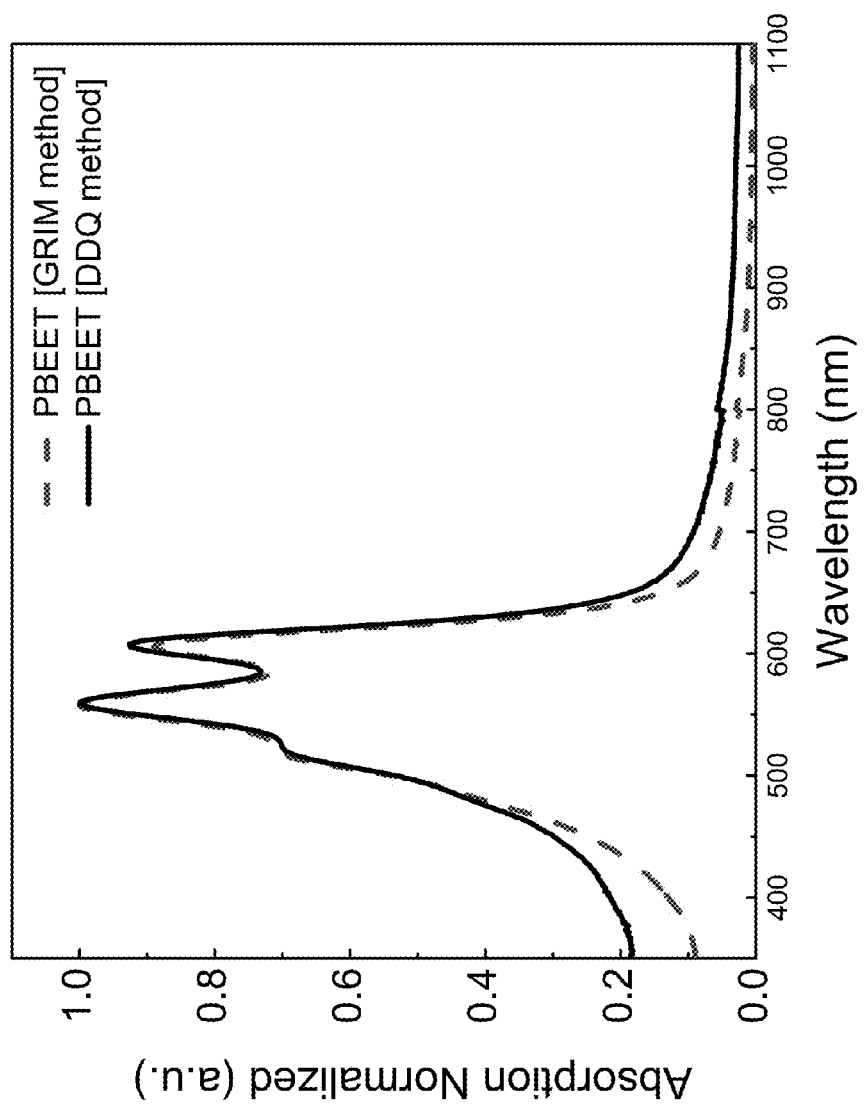
FIG. 5 shows comparative UV-Vis analysis of poly{3,4-bis[2-(2-butoxyethoxy)ethoxy]thiophene} [PdiBEET] prepared by the oxidative polymerization with DDQ (thick solid line) and the GRIM methodology (dash line).

The material characteristics of the polymers synthesized via oxidative method and GRIM method are shown in Table 4 and FIG. 5.

TABLE 1

Molecular weight and purity data for PMEET polymer samples prepared by the general procedures outlined above vs. polymers prepared by GRIM method

| # | Material (Polymer) | Method (Exp #) | GPC Data[1] $M_n$ | PDI | Purity Report[2] (ppm) Zn | Fe | Ni | Mg | Br[3] |
|---|---|---|---|---|---|---|---|---|---|
| 1 | PMEET | Oxi (1) | 17,900 | 1.9 | 0-10 | 5-10 | <0.1 | 13.2 | <48.8 |
| 2 | PMEET | Oxi (2) | 7K-18K | 1.4-7 | 10-18 | 9.2 | 0 | 3.7 | NA |
| 3 | PMEET[4] | GRIM | 15K-17K | 1.7-2.2 | 0-10 | 5-10 | 1.2-3,000 | 1.7-1,500 | 15,200 |

TABLE 2

Molecular weight and purity data for PdiBEET and P(diBEET-r-BEET) polymer samples prepared by the general procedures outlined above vs. polymers prepared by GRIM method

| # | Material (Polymer) | Method (Exp #) | GPC Data[1] $M_n$ | PDI | Purity Report[2] (ppm) Zn | Fe | Ni | Mg | Br[3] |
|---|---|---|---|---|---|---|---|---|---|
| 1 | PdiBEET | Oxi (3) | 14,400 | 1.6 | NA | NA | NA | NA | NA |
| 2 | PdiBEET | Oxi (4) | 33,800 | 1.6 | NA | NA | 1.2 | 3.8 | <113 |
| 3 | PdiBEET | Oxi (5) | 38,839 | 1.9 | 3 | 74 | 2 | 3 | NA |
| 4 | PdiBEET | Oxi (6) | 25,689 | 1.9 | 9 | 55 | 3 | 4 | NA |

TABLE 2-continued

Molecular weight and purity data for PdiBEET and P(diBEET-r-BEET) polymer samples prepared by the general procedures outlined above vs. polymers prepared by GRIM method

| # | Material (Polymer) | Method (Exp #) | GPC Data[1] | | Purity Report[2] (ppm) | | | | |
|---|---|---|---|---|---|---|---|---|---|
| | | | $M_n$ | PDI | Zn | Fe | Ni | Mg | Br[3] |
| 5 | P(diBEET-r-BEET) | Oxi (7) | 33,490 | 1.8 | 8 | 16 | 0 | 3 | NA |
| 6 | PdiBEET[4] | GRIM | 17K-31K | 1.4-2.5 | NA | NA | 12-1,500 | 22-32,000 | 3K-20K |

TABLE 3

Molecular weight and purity data for P2EF3 polymer samples prepared by the general procedures outlined above vs. polymers prepared by GRIM method

| # | Material (Polymer) | Method (Exp #) | GPC Data[1] | | Purity Report[2] (ppm) | | | | |
|---|---|---|---|---|---|---|---|---|---|
| | | | $M_n$ | PDI | Zn | Fe | Ni | Mg | Br[3] |
| 1 | P2EF3 | Oxi (8) | 3K-5.5K | 1.8-2.8 | 0-2.4 | ·4-100 | 0-1 | 1-2.2 | <48.5 |
| 2 | P2EF3[4] | GRIM | 5K-8K | 1.4-1.6 | 30-64 | 18-45 | 30-14,000 | 1-50,000 | 36K-70K |

[1]GPC data were obtained on PL-220 with NMP/LiBr (0.1 mM) as the eluent (sample [c] = 0.8 mg/mL, flow rate 0.8 mL/min, 80° C.)
[2]Purity was obtained utilizing ICP-AES/MS method (Plextronics, Inc. and R. J. Lee Group, Inc. laboratory results for metals and IC-combustion bromide analysis)
[3]Minimum and/or maximum reporting limit (IC-combustion method, R. J. Lee Group, Inc., or NAA analysis, Elemental Analysis, Inc.)
[4]GRIM methodology requires two additional steps: (a) dehalogenation and (b) metal purification step to remove Br, Mg, and Ni, respectively. These steps are introduced during polymerization or done during post-polymerization treatment of polymer. Results presented in Tables 1, 2, 3 show a range of metals and Br content for polymer batches before the dehalogenation treatment with or without metal purification steps applied [e.g., at least 30 batches of PMEET, PdiBEET, or P2EF3 prepared via GRIM method were analyzed]. Lit. Ref.: (a) Loewe, R. S.; Khersonsky, S. K.; McCullough, R. D. *Adv. Mater.* 1999, 3, 250 (GRIM method); (b) Sheina, E. E. US 2010/0273007 A1 (dehalogenation method). GRIM polymerization is described in, for example, U.S. Pat. No. 6,166,172.

TABLE 4

Exemplary materials characterization data for polymers synthesized via oxidative route and GRIM methodologies

| # | Polymer | Synthetic Method | TGA | | UV-Vis |
|---|---|---|---|---|---|
| | | | $T_{onset}$ (C. °) | Residue (%) | $\lambda_{max}$ (nm) |
| 1 | PMEET | oxidative | 287 | 0.38 | 516 |
| 2 | PdiBEET | oxidative | 320 | <1 | 536 (568) |
| 3 | P2EF3 | oxidative | 332 | 0.17 | 523 |
| 4 | P3MEET | GRIM | 324 | 0.40 | 598 |
| 5 | P3BEET | GRIM | 321 | <2 | 559 (607) |
| 6 | P2EF3 | GRIM | 326 | 2.28 | 553 |

Example 10

Preparation of Non-aqueous (NQ) Inks with 4-methyl-N-phenyl-N-(4-(phenyl(p-tolyl)amino)phenyl) benzenaminium tetrakis(pentafluorophenyl)borate [NQ-N,N-PTAPB-PB$_4$]

All steps of the preparation were carried out in inert atmosphere in a glove-box. A 2:1 mixture of methyl benzoate and 3-methoxy propionitrile was prepared by shaking the solvent together in a vial. This solvent system was combined with polymer in a separate vial, and the mixture was stirred at 80° C. for one hour. The solution was then removed from heating and allowed to cool to room temperature for fifteen minutes. Next, NQ-N,N-PTAPB-PB$_4$ was added to a 2:1 mixture of methyl benzoate and 3-methoxy propionitrile in a separate vial from the polymer solution, and the mixture was stirred for 15 minutes. The solution was then added dropwise over two minutes to the stirred solution of the polymer. After the addition was complete, the mixture is stirred for thirty minutes at 50° C. The solution was then allowed to sit at room temperature for thirty minutes before filterability tests were performed.

Example 11

Preparation of Inks Non-aqueous (NQ) Inks with tetrakis(pentafluorophenyl)borate [NQ-PB$_4$]

All steps of the preparation were carried out in inert atmosphere in a glove-box. To a clean vial the polymer was added. Next dry solvent was added and the mixture was stirred at ambient temperature until the polymer dissolved producing a magenta colored solution. To a second clean vial, NQ-PB$_4$ was added along with dry solvent. The contents were mixed until a clear solution formed. The dopant solution was added drop-wise with stirring to the polymer solution. During the addition, the color of the polymer solution changed from magenta to dark blue. The mixture was then warmed to 50° C. for 3 days. After this time the mixture was allowed to cool to room temperature and filtered through a 0.45 micron PTFE filter. The filtered ink was stored in an amber vial in the glove-box.

Example 12

Hole-Only Device (HOD)

Device Fabrication

The hole only device is a unipolar device wherein the hole only injection efficiency of the HIL into the HTL was studied. The hole only devices to test the hole injection were fabricated on indium tin oxide (ITO) surfaces deposited on glass substrates. The ITO surface was pre-patterned to define the pixel area of 0.09 cm$^2$. The device substrates were cleaned by ultrasonication in a dilute soap solution for 20 minutes each followed by distilled water washes. This was followed by ultrasonication in isopropanol for 20 minutes. The substrates were dried under nitrogen flow, following which they were treated in a UV-Ozone chamber operating at 300 W for 20 minutes.

The cleaned substrates were then coated with an HIL ink and dried at 90-170° C. for 5-15 minutes to form an HIL layer. Dry film thicknesses ranged from approximately 20 nm to 60 nm. The coating process was done on a spin coater but can be similarly achieved with spray coating, ink-jetting, contact printing or any other deposition method capable of resulting in an HIL film of the desired thickness. The substrates were then transferred to a vacuum chamber where the remaining layers of the device stack were deposited by means of physical vapor deposition. For hole only device fabrication, N,N' (di naphthalen-1-yl)-N,N'-diphenyl-benzidine (NPB) a hole transporting layer (HTL) was deposited on top of the HIL followed by a Gold (Au) cathode.

Device Testing

The hole only devices comprise pixels on a glass substrate whose electrodes extended outside the encapsulated area of the device which contain the light emitting portion of the pixels. The typical area of each pixel is 0.09 cm$^2$. The electrodes were contacted with a current source meter such as a Keithley 2400 source meter with a bias applied to the indium tin oxide electrode while the gold electrode was earthed. This results in positively charged carriers (holes) being injected into the device. In this example, the HIL assists the injection of charge carriers into the hole transporting layer. This resulted in a low operating voltage of the device (defined as the voltage required to run a given current density through the pixel).

Figure 6:
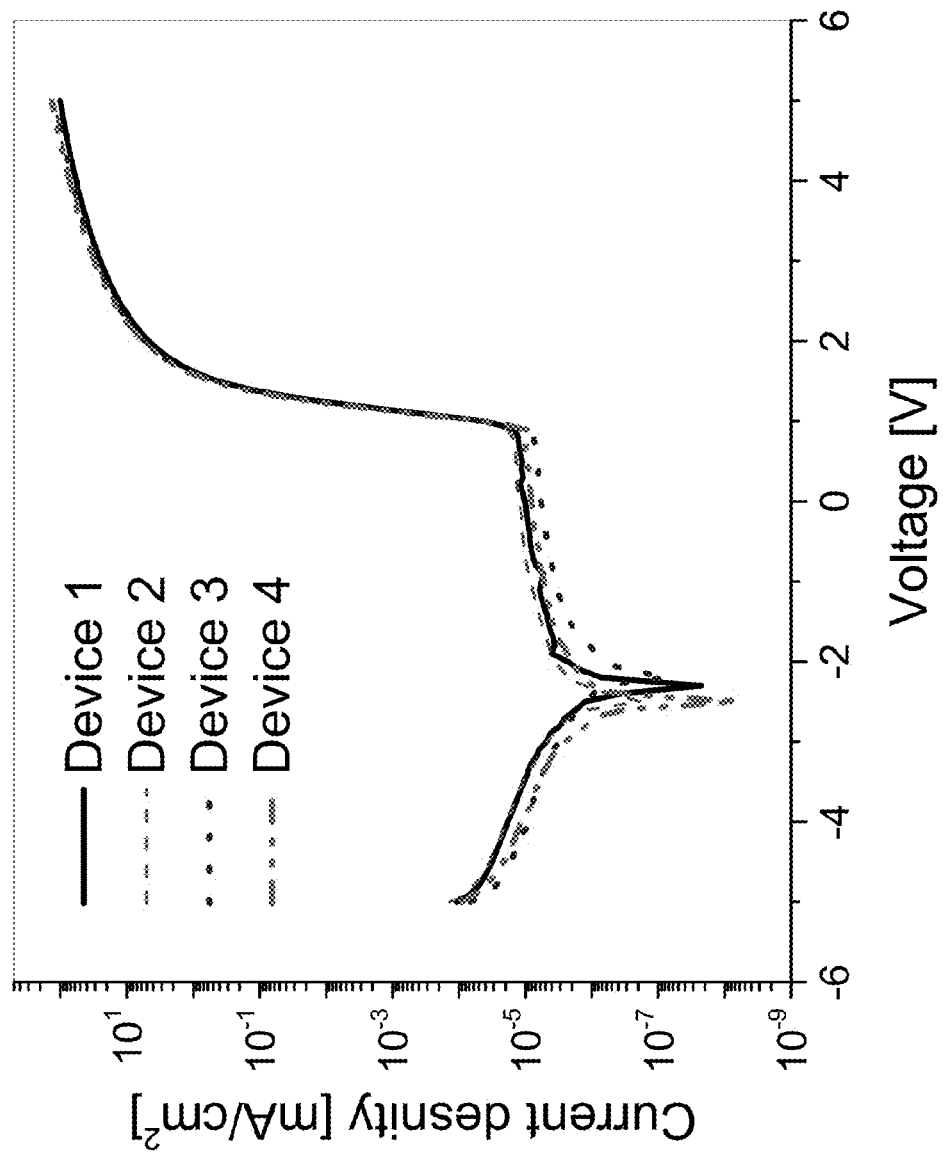
FIG. 6 shows performance of hole-only devices according to exemplary embodiments described herein.
Figure 7:
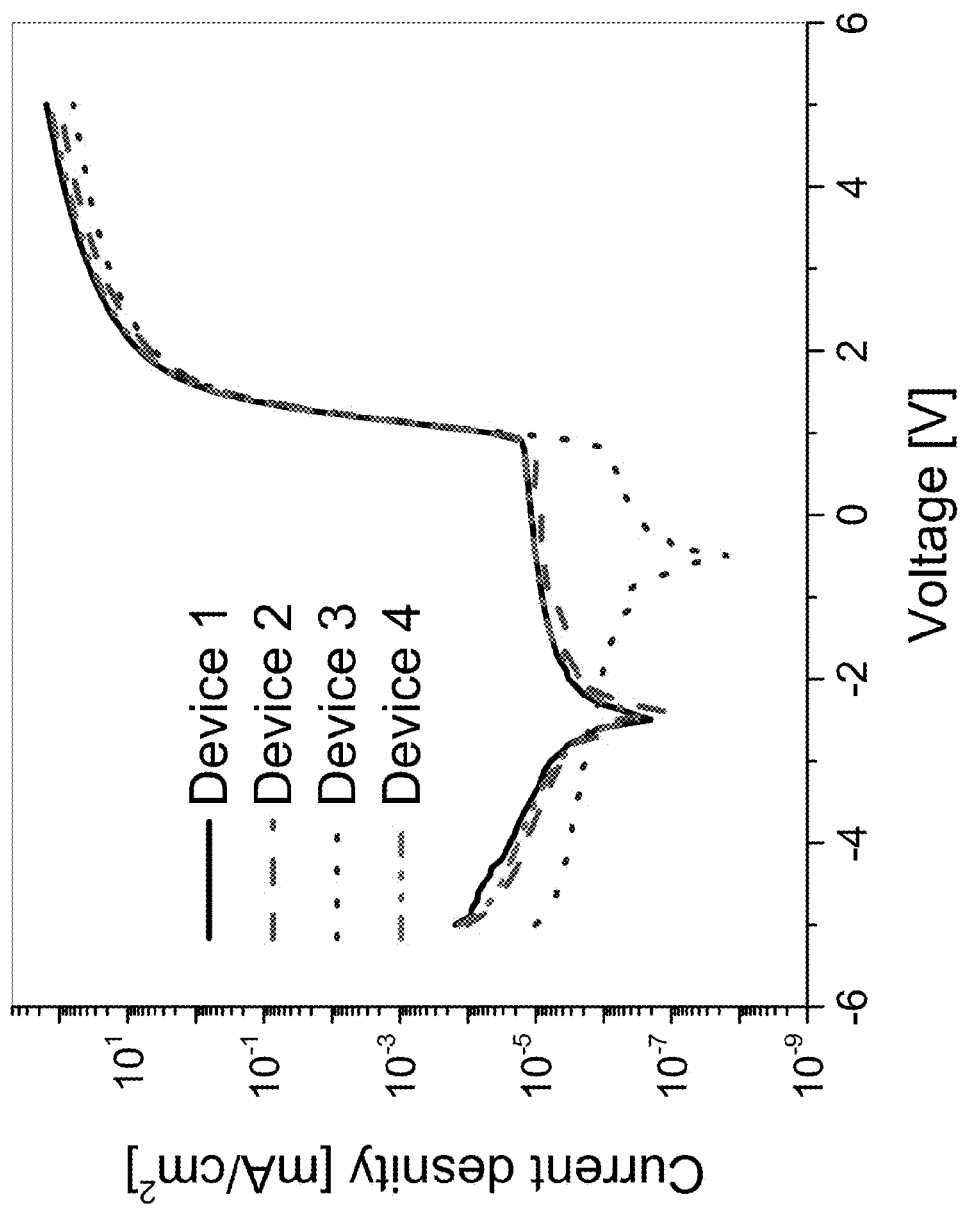
FIG. 7 shows performance of hole-only devices according to exemplary embodiments described herein.
Figure 8:
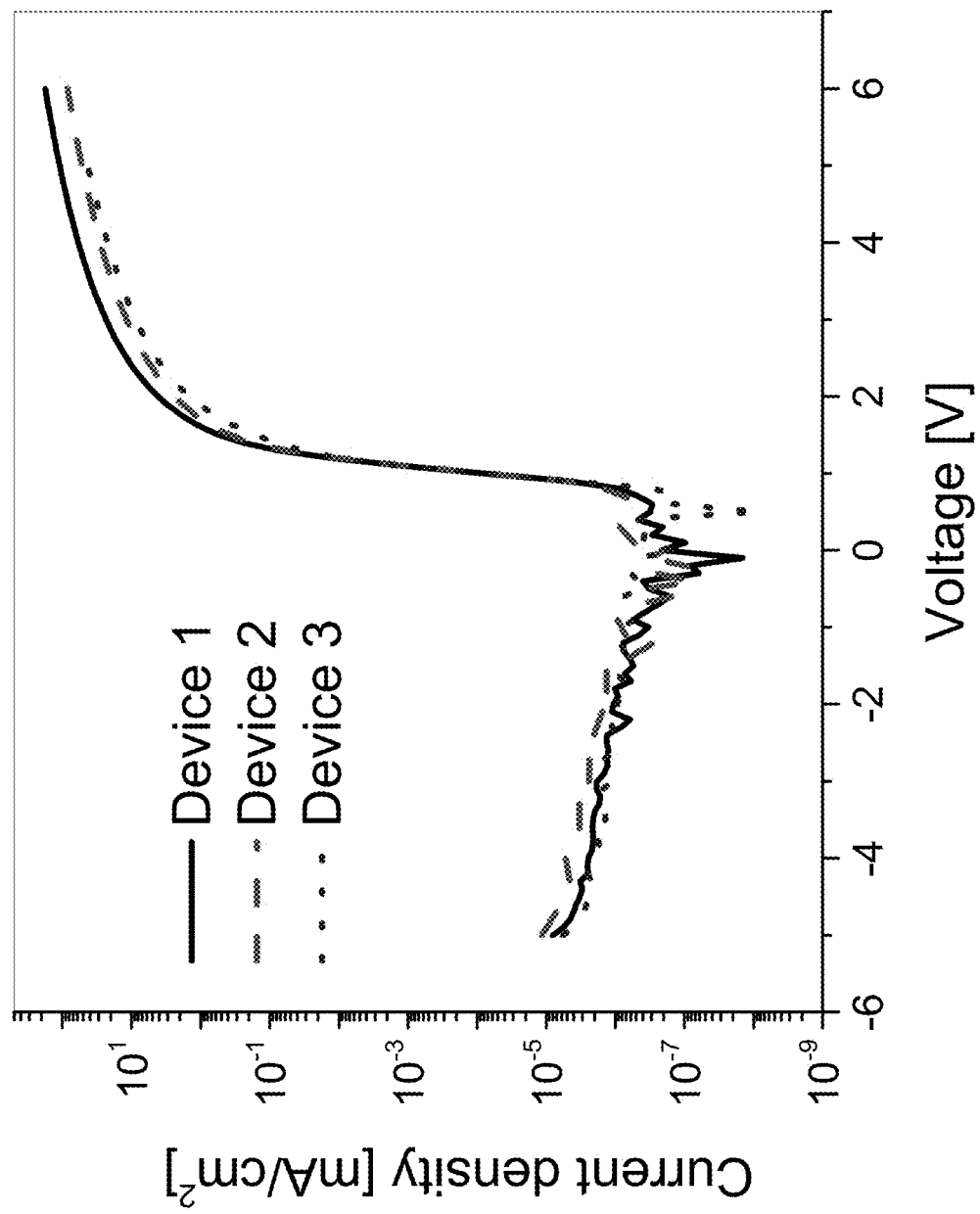
FIG. 8 shows performance of hole-only devices according to exemplary embodiments described herein.

As shown in Tables 5-7 and FIGS. 6-8, polythiophene-based polymers produced by oxidative polymerization showed equivalent or better HOD results that are within typical statistical variation observed in HOD devices based on polymers produced by traditional GRIM method, indicating that all polymer batches deliver HILs with similar level of injection. Voltage is measured at 10 mA/cm$^2$.

TABLE 5

Exemplary HOD device data containing HILs formulated from NQ-NN-PTAPB-PB$_4$ and PdiBEET polymers synthesized via oxidative route and GRIM methodologies (see FIG. 6 for plot of current density against voltage)

| Device # | Ink Formulation | Polymer | Synthetic Method | Voltage (V) |
|---|---|---|---|---|
| 1 | NQ-NN-PTAPB-PB$_4$ | PdiBEET | GRIM | 2.32 ± 0.05 |
| 2 | NQ-NN-PTAPB-PB$_4$ | PdiBEET | GRIM | 2.25 ± 0.02 |
| 3 | NQ-NN-PTAPB-PB$_4$ | PdiBEET | oxidative | 2.25 ± 0.02 |
| 4 | NQ-NN-PTAPB-PB$_4$ | PdiBEET | oxidative | 2.28 ± 0.06 |

TABLE 6

Exemplary HOD device data containing HILs formulated from NQ-NN-PTAPB-PB$_4$ and P(diBEET-r-BEET) copolymers synthesized via oxidative route and GRIM methodologies (see FIG. 7 for plot of current density against voltage)

| Device # | Ink Formulation | Polymer | Synthetic Method | Voltage (V) |
|---|---|---|---|---|
| 1 | NQ-NN-PTAPB-PB$_4$ | PdiBEET* | GRIM | 2.22 ± 0.05 |
| 2 | NQ-NN-PTAPB-PB$_4$ | P(diBEET-r-BEET) | GRIM | 2.35 ± 0.02 |
| 3 | NQ-NN-PTAPB-PB$_4$ | P(diBEET-r-BEET) | GRIM | 2.51 ± 0.05 |
| 4 | NQ-NN-PTAPB-PB$_4$ | P(diBEET-r-BEET) | oxidative | 2.26 ± 0.04 |

Note:
device 3, as shown in FIG. 7, showed a higher voltage, which can be a disadvantage for a HOD measurement. Voltage is measured at 10 mA/cm$^2$.

TABLE 7

Exemplary HOD device data containing HILs formulated from NQ-PB$_4$ and P(diBEET-r-BEET) copolymers synthesized via oxidative route and GRIM methodologies (see FIG. 8 for plot of current density against voltage)

| Device # | Ink Formulation | Polymer | Synthetic Method | Voltage (V) |
|---|---|---|---|---|
| 1 | NQ-PB$_4$ | PdiBEET* | GRIM | 2.39 ± 0.06 |
| 2 | NQ-PB$_4$ | P(diBEET-r-BEET) | oxidative | 2.91 ± 0.11 |
| 3 | NQ-PB$_4$ | P(diBEET-r-BEET) | GRIM | 3.13 ± 0.28 |

*Control HOD device based on HIL prepared from PdiBEET made via GRIM.

What is claimed is:

1. A method comprising:
polymerizing by oxidative chemical polymerization at least one first monomer in the presence of at least one organic oxidant, wherein the first monomer comprises at least one optionally substituted heterocyclic ring, wherein the heterocyclic ring comprises at least one heteroatom, wherein the polymerizing is carried out with a separate Lewis acid also present.

2. The method of claim 1, wherein the first monomer consists of one optionally substituted heterocyclic ring.

3. The method of claim 1, wherein the first monomer comprises at least two optionally substituted heterocyclic rings.

4. The method of claim 1, wherein the first monomer comprises at least two optionally substituted fused heterocyclic rings.

5. The method of claim 1, wherein the heteroatom is O, S, or N.

6. The method of claim 1, wherein the first monomer is represented by:

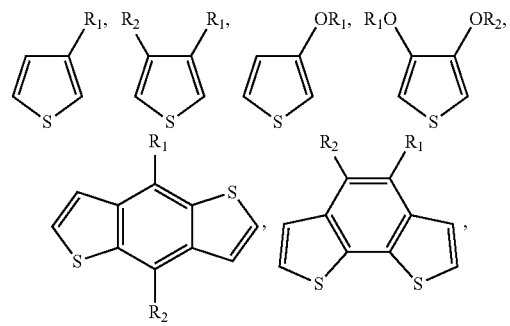

-continued

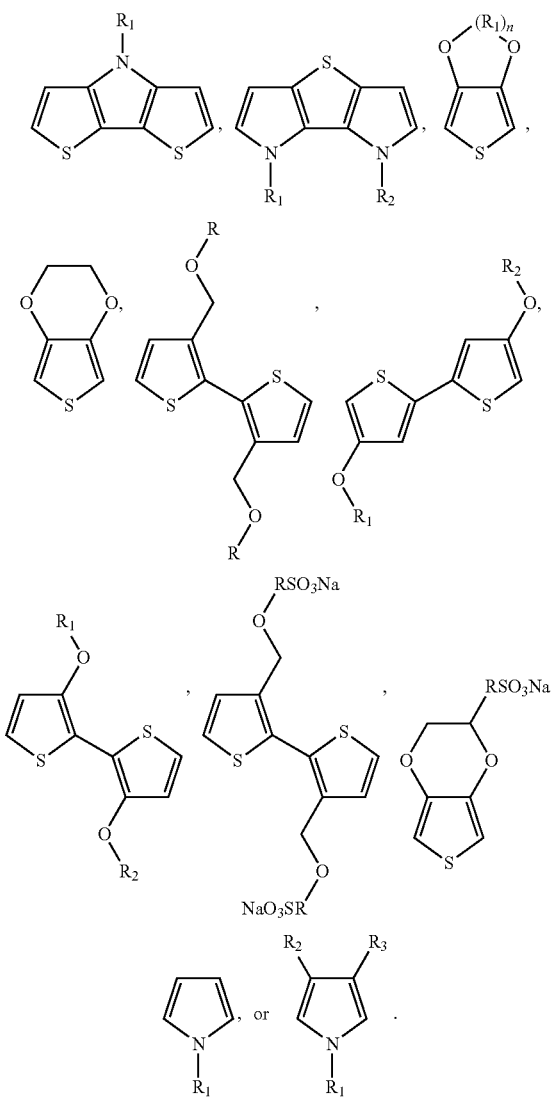

wherein R, $R_1$, $R_2$, and $R_3$ are each a hydrogen or an optionally substituted linear, branched or cyclic alkyl, aryl, alkoxy, aryloxy, alkylthio, arylthio, acyl, ether, or polyether.

7. The method of claim 1, wherein the first monomer is represented by:

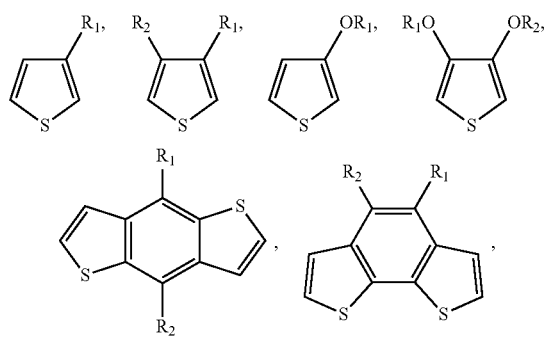

-continued

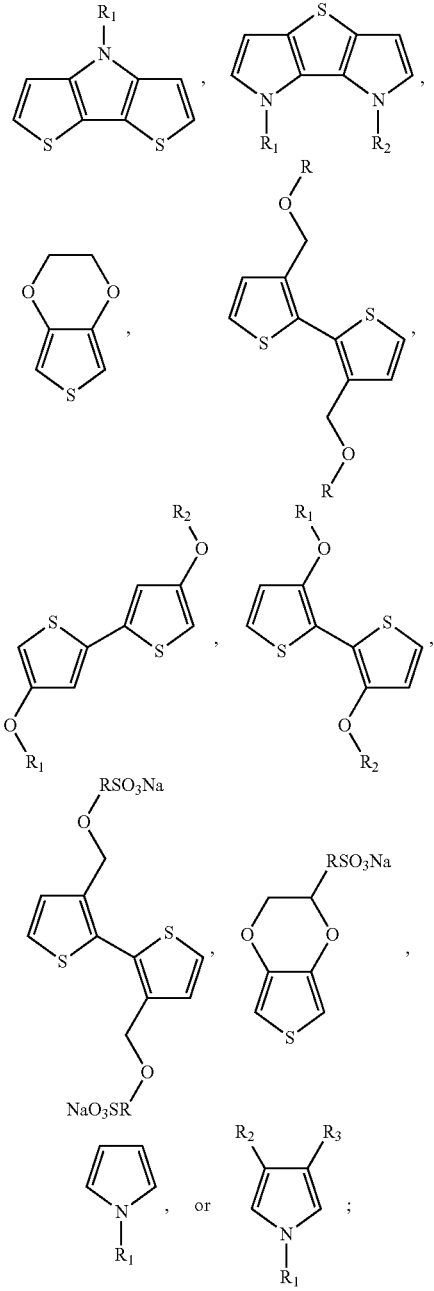

wherein R, $R_1$, $R_2$, and $R_3$ are each independently a linear or branched alkyl, alkoxy, ether or polyether, or together a cyclic alkyl, alkoxy, ether or polyether.

8. The method of claim 1, wherein the first monomer is a substituted thiophene.

9. The method of claim 1, wherein the first monomer is a 3-substituted thiophene.

10. The method of claim 1, wherein the first monomer is a 3,4-substituted thiophene.

11. The method of claim 1, wherein the first monomer is a dimer comprising a first optionally substituted thiophene unit and a second optionally substituted thiophene unit.

12. The method of claim 1, wherein the first monomer is free of any halogen substituents.

13. The method of claim 1, wherein the first monomer is free of any polymerizable halogen group directly bonded to the heterocyclic ring.

14. The method of claim 1, wherein the first monomer comprises at least one polyether substituent.

15. The method of claim 1, wherein the first monomer comprises at least one alkoxy substituent.

16. The method of claim 1, wherein the organic oxidant comprises an optionally substituted quinone group.

17. The method of claim 1, wherein the organic oxidant comprises an optionally substituted quinonimine group or an optionally substituted quinondiimine group.

18. The method of claim 1, wherein the organic oxidant comprises an optionally substituted nitroarene group.

19. The method of claim 1, wherein the organic oxidant is represented by formula (I), (II), or (III):

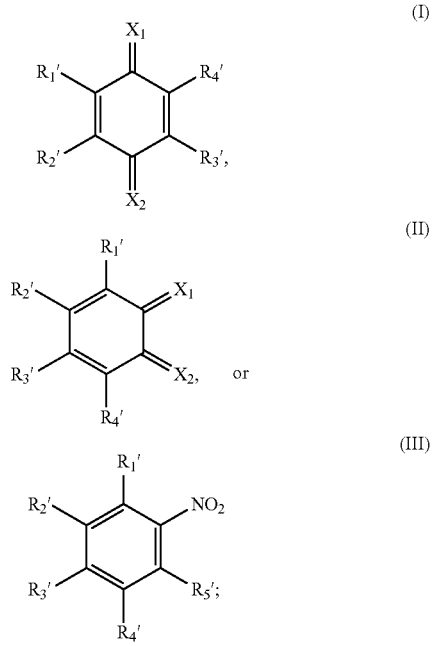

wherein $X_1$ and $X_2$ are each independently O or N—$R_6'$, and wherein $R_1'$, $R_2'$, $R_3'$, $R_4'$, $R_5'$ and $R_6'$ are each independently a hydrogen, a halogen, or an optionally substituted linear, branched, or cyclic alkyl, alkenyl, alkynyl, alkoxy, alkylthio, ester, ketone, carboxylic acid, carboxylate ester, nitro, sulfonic acid, sulfonate ester, sulfonic acid amide, or cyano group.

20. The method of claim 1, wherein the organic oxidant is 2,3-dichloro-5,6-dicyanobenzoquinone (DDQ).

21. The method of claim 1, wherein the Lewis acid comprises $BF_3$.

22. The method of claim 1, wherein the polymerizing is carried out in the presence of at least one solvent.

23. The method of claim 1, wherein the polymerizing is carried out substantially in absence of any solvent.

24. The method of claim 1, wherein the polymerizing step is carried out in a reaction mixture, wherein the reaction mixture further comprises a second monomer different from the first monomer.

25. The method of claim 1, wherein the polymerizing step is carried out in a reaction mixture, wherein the reaction mixture further comprises a second monomer different from the first monomer, wherein the first monomer is 3,4-disubstituted thiophene, and wherein the second monomer is 3-substituted thiophene.

26. The method of claim 1, further comprising quenching the reaction with an organometallic quenching agent, a metal quenching agent, or an organic quenching agent.

27. The method of claim 1, further comprising quenching the reaction with at least one metallocene.

28. The method of claim 1, further comprising quenching the reaction with zinc.

29. The method of claim 1, wherein the polymerizing step produces a conjugated polymer, the method further comprising dedoping the conjugated polymer with at least one reducing agent.

30. The method of claim 1, wherein the polymerizing step produces a conjugated polymer, the method further comprising dedoping the conjugated polymer with hydrazine.

31. The method of claim 1, wherein the polymerizing is carried out substantially free of any metal-based oxidant or metal-based catalyst.

32. The method of claim 1, wherein the polymerization is carried out without a Brönsted acid.

33. The method of claim 1, wherein the polymerization is carried out substantially in absence of any proton source.

34. The method of claim 1, wherein the first monomer does not comprise a halogen bonded to the heterocyclic ring, and wherein polymerization is carried out without a metal oxidant, initiator, or catalyst.

35. The method of claim 34, wherein the polymerizing step produces a polymer having an Mn of at least 1,000 g/mol.

36. The method of claim 1, wherein the Lewis acid comprises at least one $BF_3$ etherate.

37. The method of claim 36, wherein the $BF_3$ etherate is $BF_3 \cdot (C_2H_5)_2O$.

38. The method of claim 1, wherein the polymerizing step produces a polymer, and after polymerization, the polymer is not subjected to a dedoping step.

39. The method of claim 1, wherein the polymerizing is carried out and the resulting polymer is not subjected to a dedoping step.

40. The method of claim 1, wherein the first monomer comprises at least three optionally substituted heterocyclic rings.

41. The method of claim 1, wherein the heterocyclic ring is a five-member ring comprising at least one heteroatom, and the heteroatom is S or N.

42. The method of claim 1, wherein the first monomer comprises at least one fluorinated substituent.

* * * * *